(12) United States Patent
Hallahan et al.

(10) Patent No.: US 6,998,471 B2
(45) Date of Patent: Feb. 14, 2006

(54) **POLYNUCLEOTIDES ENCODING AN ACETYL-COA ACETYLTRANSFERASE FROM *HEVEA BRASILIENSIS*, RELATED PRODUCTS, AND METHODS**

(75) Inventors: David L. Hallahan, Wilmington, DE (US); Natalie M. Keiper-Hrynko, Bear, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 56 days.

(21) Appl. No.: 10/036,959

(22) Filed: Jan. 2, 2002

(65) Prior Publication Data

US 2003/0119098 A1 Jun. 26, 2003

Related U.S. Application Data

(60) Provisional application No. 60/307,673, filed on Jul. 25, 2001.

(51) Int. Cl.
| | | |
|---|---|---|
| C07H 21/04 | (2006.01) | |
| C12N 1/20 | (2006.01) | |
| C12N 15/00 | (2006.01) | |
| C12N 1/14 | (2006.01) | |
| C12N 5/04 | (2006.01) | |

(52) U.S. Cl. .................. 536/23.2; 536/23.6; 435/252.3; 435/320.1; 435/254.11; 435/419; 435/325

(58) Field of Classification Search .............. 536/23.2, 536/23.6; 435/320.1, 252.3, 254.11, 419, 435/325, 440, 468
See application file for complete search history.

(56) References Cited

U.S. PATENT DOCUMENTS

| | | | |
|---|---|---|---|
| 6,316,695 B1 | 11/2001 | Han et al. | |
| 6,319,710 B1 | 11/2001 | Olafsdottir et al. | ......... 435/325 |
| 6,689,582 B1 | 2/2004 | Davies et al. | ............. 435/69.1 |

FOREIGN PATENT DOCUMENTS

| | | |
|---|---|---|
| EP | 0955363 A2 | 4/1999 |
| EP | 1033405 A2 | 9/2000 |
| WO | WO 00/53782 | 9/2000 |
| WO | WO 01/31027 A1 | 5/2001 |

OTHER PUBLICATIONS

Ngo et al. Computational Complexity, Protein Structure Prediction, and the Levinthal Paradox. (1994) Merz et al. (Ed), Birkhauser, Boston, MA pp. 433 and 492-495.*
Tanaka, Y. , In Rubber and Related Polyprenols. Methods in Plant Biochemistry; Dey, P. M. and Harborne, J. B., Eds., Academic Press: San Diego, 1991; vol. 7, pp 519-536.
Charlwood et al, In Minor Classes of Terpenoids. Methods in Plant Biochemistry; Dey, D. M> and Harborne, J. B., Eds., Academic Press; San Diego, 1991; vol. 7, pp. 537-542.
Lichtenthaler et al., Physiol. Plantarum 101: 643-652, 1997.
Lichtenthaler et al., FEBS Letts. 400: 271-274, 1997.
Newman, J. D., Chappell, J. , Isoprenoid biosynthesis in plants: carbon partitioning within the cytoplasmic pathway. Crit Rev. Biochem. Mol. Biol. 1999; 34(2): 95-106.
Bach et al. Mevalonate biosynthesis in plants. Crit Rev. Biochem. Mol. Biol. 1999; 34(2): pp. 107-122.
Han et al., Tree Physiol. 20: 503-510, 2000.
Oh et al., J. Plant Physiol. 157: 549-557, 2000.
McGarvey et al., Plant Cell 7:1015-1026, 1995.
Chappell, J., Annyu. Rev. Plant Physiol. Plant Mol. Biol. 46:521-547, 1995.
Alex, D., Bach, T. J. and Chye, M. L. Expression of *Brassica juncea* 3-hydroxy-3-methylglutaryl CoA synthase is developmentally regulated and stress-responsive. Plant J. 22(5), 415-426, 2000.
Chye, M. L. et al., Characterization of cDNA and genomic clones encoding 3-hydroxy-3methylglutaryl-coenzyme. A reductase from *Hevea brasiliensis*. Plant Mol. Biol. 16(4), 567-577, 1991.
Riou, C., et al., Isolation and characterization of cDNA encoding *Arabidopsis thaliana* mevalonate kinase by genetic complementation in yeast. Gene 148 (2), 293-297, 1994.
Sato, S., et al., Structual analysis of Arabidopsis thaliana chromosome 5. X. Sequence features of the regions of 3,076,755 bp covered y sixty P1 and TAC clones. DNA Res. 7(1), 31-63, 2000.
Cordier et al., Heterologous expression in *Saccharomyces cerevisiae* of an *Arabidopsis thaliana* cDNA encoding mevalonate diphosphate decarboxylase. Plant Mol. Biol. 39(5), 953-967, 1999.
Oh et al., Molecular Cloning, Expression, and Functional Analysis of a cis-Prenyltransferase from *Arabidopsis thaliana*, The Journal of Biological Chemistry, vol. 275, No. 24, Jun. 16, 2000, pp. 18482-18488.
*Hevea brasiliensis* hydroxymethylglutaryl coenzyme A synthase mRNA, complete cds. Accession No. AF396829, Jul. 2001.
Suwanmanee et al., Regulation of the Expression of 3-hydroxy-3-methylglutaryl CoenzymeA (HMG-Co) synthase gene in *Hevea brasiliensis*, 2000, Biochemical Society Transactions vol. 28, Part 5, 1838.

(Continued)

*Primary Examiner*—Tekchand Saidha
(74) *Attorney, Agent, or Firm*—Morgan & Finnegan, L.L.P.

(57) ABSTRACT

The instant invention relates to bioproduction of isopentenyl diphosphate within the latex of the rubber tree, *Hevea brasiliensis*. Isopentenyl diphosphate (IPP) synthesis from acetate is mediated by a set of enzymes, acetyl-coA acetyltransferase, HMG-coA synthase, HMG-coA reductase, mevalonate kinase, phosphomevalonate kinase and mevalonate diphosphate decarboxylase, encoded by six genes isolated as expressed sequence tag (EST) cDNAs from *Hevea brasiliensis* latex. In addition, a variant sequence of one of these enzymes, acetyl-coA acetyltransferase, has been found.

10 Claims, 2 Drawing Sheets

OTHER PUBLICATIONS

Palmer et al., "Biosynthetic Thiolase from *Zoogloea ramigera*," J. Biol. Chem., 1991, 266: 8369-8375.

Kyte, J. and Doolittle, R.F., "A Simple Method for Displaying the Hydropathic Character of a Protein," J. Mol. Biol., vol. 157, p. 105-132, 1982.

Mathieu, M., et al, "The 2.8A crystal structure of peroxisomal 3-ketoacyl-CoA thiolase of *Saccharomyces cervisiae*: a five-layered αβαβα structure constructed from two core domains of identical topology," Structure, vol. 2, No. 9, p. 797-808, 1994.

Weber, T. et al, "Conversion of acetyl-coenzyme A into 3-hydroxy-3-methylglutaryl-coenzyme A in radish seedlings. Evidence of a single monomeric protein catalyzing a FeII/quinone-stimulated double condensation raction," Biochimica et Biophysica Acta, vol. 1211, p. 85-96, 1994.

Supplementary Partial European Search Report for European Patent Application EP 02 75 2612, issued Mar. 7, 2005; European Patent Office.

Chye, M.-L. et al., "Characterization of cDNA and genomic clones encoding 3-hydroxy-3-methylglutaryl-coenzyme A reductase from *Hevea brasiliensis*," Plant Molecular Biology, vol. 16, pp. 567-577, 1991.

Han, K.-H. et al., "Genes expressed in the latex of *Hevea brasiliensis*," Tree Physiology, vol. 20, pp. 503-510, Apr. 2000.

Mee-Len Chye et al, "Three genes encode 3-hydroxy-3-methylglutaryl-coenzyme A reductase in *Hevea brasiliensis*: hmg1 and hmg3 are differentially expressed"Plant Molecular Biology, vol. 19, pp 473-484, 1992.

X. Deng, "The 5' end promoter region of the rubber elongation factor,"NCBI, gi: 14211501, May 28, 2001.

P. Arokiaraj et al., "Isolation of putatitive regulatory sequence in the 5' upstream region of hevein (HEVI) of rubber tree (*Hevea brasiliensis*)" NCBI, gi: 10304329, Sep. 26, 2000.

Vollack et al., "Cloning of a cDNA Encoding Cytosolic Acetoacetyl-Coenzyme A Thiolase from Radish by Functional Expression in Saccharomyces cerevisiae"Plant Physiol., 1996, vol. 111, pp. 1097-1107.

* cited by examiner

POLYNUCLEOTIDES ENCODING AN ACETYL-COA ACETYLTRANSFERASE FROM *HEVEA BRASILIENSIS*, RELATED PRODUCTS, AND METHODS

This application claims benefit of U.S. Provisional Application No. 60/307,673, filed Jul. 25, 2001.

FIELD OF THE INVENTION

The present invention relates to the field of molecular biology and botany. More specifically, this invention pertains to nucleic acid fragments encoding enzymes useful for the bioproduction of isopentenyl diphosphate.

BACKGROUND OF THE INVENTION

Plants synthesize a variety of hydrocarbons built up of isoprene units ($C_5H_8$), termed polyisoprenoids (Tanaka, Y. In *Rubber and Related Polyprenols. Methods in Plant Biochemistry*; Dey, P. M. and Harborne, J. B., Eds., Academic Press: San Diego, 1991; Vol. 7, pp 519–536). Those with from 45 to 115 carbon atoms, and varying numbers of cis- and trans- (Z- and E-) double bonds, are termed polyprenols, while those of longer chain length are termed rubbers (Charlwood et al., In *Minor Classes of Terpenoids. Methods in Plant Biochemistry*; Dey, P. M. and Harborne, J. B., Eds., Academic Press: San Diego, 1991; Vol. 7, pp 537–542). The synthesis of these compounds is carried out by a family of enzymes termed prenyltransferases, which catalyze the sequential addition of $C_5$ isopentenyl diphosphate units to an initiator molecule (FIG. 1). In *Hevea brasiliensis* rubber, the $C_5$ units are added in the cis-configuration, and thus the prenyltransferas(s) involved are termed cis- or Z-prenyltransferases.

Two distinct pathways for the synthesis of isopentenyl diphosphate (IPP) are now known to be present in living organisms (Lichtenthaler et al., *Physiol. Plantarum* 101: 643–652 (1997)). In one pathway, which is confined in plants to plastids, glyceraldehyde 3-phosphate and pyruvate are precursors of IPP (Lichtenthaler et al., *FEBS Letts.* 400:271–274 (1997)). In the second (cytoplasmic) pathway, acetate is converted to IPP via the intermediate mevalonic acid (Newman, J. D., Chappell, J. Isoprenoid biosynthesis in plants: carbon partitioning within the cytoplasmic pathway. *Crit Rev Biochem Mol Biol.* 1999;34(2):95–106; Bach T J, Boronat A, Campos N, Ferrer A, Vollack K U, Mevalonate biosynthesis in plants. *Crit Rev Biochem Mol Biol.* 1999;34 (2): 107–22). The latter pathway, the acetate/mevalonate pathway, has long been assumed to be the sole pathway operating in the rubber-synthesizing latex of *Hevea brasiliensis*. In this pathway, acetate is converted to IPP by the sequential action of the following six enzymes: acetyl-coA acetyltransferase, HMG-coA synthase, HMG-coA reductase, mevalonate kinase, phosphomevalonate kinase and mevalonate diphosphate decarboxylase (FIG. 2).

Of the minimum of six genes encoding the enzymes of this pathway in *Hevea brasiliensis*, only those for HMG-coA reductase have been cloned. Two cDNAs, encoding enzymes termed HMGR1 and HMGR2, were isolated using a heterologous hybridization probe, and genomic southern blotting confirmed the presence of at least two genes for HMG-coA reductase in the *Hevea brasiliensis* genome (Chye et al., *Plant Mol. Biol.* 16:567–577 (1991)). An EST homologous with HMGR1 was also identified in a *Hevea brasiliensis* latex library (Han et al., *Tree Physiol.* 20:503–510 (2000)). A gene encoding a third isoform of HMG-coA reductase in Hevea, termed HMGR3, has also been reported (Chye et al (1992) *Plant Mol. Biol.* 19: 473–484). Of the other five genes, although several have been identified in other plant species, no *Hevea brasiliensis* homologs have been identified or their genes isolated.

The initiator molecules used for the elaboration of polyprenols and rubbers are also derived from IPP, and are allylic terpenoid diphosphates such as dimethylallyldiphosphate (DMAPP), but more usually the $C_{10}$ compound geranyl diphosphate (GPP), the $C_{15}$ compound farnesyl diphosphate (FPP) or the $C_{20}$ compound geranylgeranyl diphosphate (GGPP) (FIG. 1). DMAPP is generated from IPP by the action of an isomerase enzyme termed IPP isomerase. Genes encoding this enzyme have been isolated from a number of species, including *Hevea brasiliensis* (Oh et al., *J. Plant Physiol.* 157:549–557 (2000)). The allylic diphosphates GPP, FPP and GGPP are synthesized by trans- or E-prenyltransferases, using DMAPP and IPP. Genes encoding the enzymes which synthesize these allylic terpenoid diphosphates have been cloned from a number of organisms, including plants (McGarvey et al., *Plant Cell* 7:1015–1026 (1995); Chappell, J., *Annu. Rev. Plant Physiol. Plant Mol. Biol.* 46:521-547 (1995)). All of these gene products condense isoprene units in the trans-configuration.

There are several suggested functions for plant polyisoprenoids. Terpenoid quinones are most likely involved in photophosphorylation and respiratory chain phosphorylation. Rubbers have been implicated in plant defense against herbivory, possibly serving to repel and entrap insects and seal wounds in a manner analogous to plant resins. The roles of the $C_{45}$–$C_{115}$ polyprenols remain unidentified, although as with most secondary metabolites they too most likely function in plant defense. Short-chain polyprenols may also be involved in protein glycosylation in plants, by analogy with the role of dolichols in animal metabolism.

The problem to be solved is to provide a pathway for the synthesis of poly-cis-isoprenoids (rubbers). Applicants have solved the stated problem by the discovery of unknown genes (except for HMG-coA reductase) for each step of the acetate/mevalonate biosynthetic pathway in latex of *Hevea brasiliensis*. More specifically, the instant invention pertains to the identification and characterization of EST sequences from *Hevea brasiliensis* latex encoding acetyl-coA acetyltransferase, HMG-coA synthase, mevalonate kinase, phosphomevalonate kinase and mevalonate diphosphate decarboxylase. A shorter variant of putative acetyl co-A acetyltransferase has also been identified.

SUMMARY OF THE INVENTION

The present invention provides an isolated nucleic acid molecule encoding an isopentenyl diphosphate biosynthesis enzyme, selected from the group consisting of:
 (a) an isolated nucleic acid molecule encoding the amino acid sequence set forth in SEQ ID NO:8, SEQ ID NO:9, SEQ ID NO:11, SEQ ID NO:12 and SEQ ID NO:13;
 (b) an isolated nucleic acid molecule that hybridizes with (a) under the following hybridization conditions: 0.1×SSC, 0.1% SDS at 65° C., and washed with 2×SSC, 0.1% SDS followed by 0.1×SSC, 0.1% SDS; and
 (c) an isolated nucleic acid molecule that is completely complementary to (a) or (b).

Additionally the invention provides chimeric genes comprising the instant nucleic acid fragments operably linked to appropriate regulatory sequences and polypeptides encoded by the present nucleic acid fragments and chimeric genes.

The invention additionally provides transformed hosts comprising the instant nucleic acid sequences wherein the host cells are selected from the group consisting of bacteria, yeast, filamentous fungi, algae and green plants.

In another embodiment the invention provides a method of obtaining a nucleic acid molecule encoding an isopentenyl diphosphate biosynthesis enzyme comprising:

(a) probing a genomic library with the nucleic acid molecule of any one of the present isolated nucleic acid sequences;

(b) identifying a DNA clone that hybridizes with the nucleic acid molecule of any one of the present nucleic acid sequences; and (c) sequencing the genomic fragment that comprises the clone identified in step (b), wherein the sequenced genomic fragment encodes an isopentenyl diphosphate biosynthesis enzyme.

Similarly the invention provides a method of obtaining a nucleic acid molecule encoding an isopentenyl diphosphate biosynthesis enzyme comprising:

(a) synthesizing at least one oligonucleotide primer corresponding to a portion of the sequence selected from the group consisting of SEQ ID NO:1, SEQ ID NO:2, SEQ ID NO:4, SEQ ID NO:5 and SEQ ID NO:6; and (b) amplifying an insert present in a cloning vector using the oligonucleotide primer of step (a);

wherein the amplified insert encodes a portion of an amino acid sequence encoding an isopentenyl diphosphate biosynthesis enzyme.

In another embodiment the invention provides a method for the production of a compound in the isopentenyl diphosphate pathway comprising: contacting a transformed host cell under suitable growth conditions with an effective amount of a carbon substrate whereby a compound in the isopentenyl diphosphate pathway is produced, said transformed host cell comprising a set of nucleic acid molecules encoding SEQ ID NO:1, SEQ ID NO:2, SEQ ID NO:4, SEQ ID NO:5 and SEQ ID NO:6 under the control of suitable regulatory sequences.

In an alternate embodiment the invention provides a method of regulating isopentenyl diphosphate biosynthesis in an organism comprising, over-expressing at least one isopentenyl diphosphate gene selected from the group consisting of SEQ ID NO:1, SEQ ID NO:2, SEQ ID NO:4, SEQ ID NO:5 and SEQ ID NO:6 in an organism such that isopentenyl diphosphate is altered in the organism. The regulation of isopentenyl diphosphate biosynthesis may be accomplished by means of expressing genes on a multicopy plasmid, operably linking the relevant genes to regulated or inducible promoters, by antisense expression or by selective disruption of certain genes in the pathway.

Additionally the invention provides mutated genes encoding an isopentenyl diphosphate biosynthesis enzyme having an altered biological activity produced by a method comprising the steps of:

(i) digesting a mixture of nucleotide sequences with restriction endonucleases wherein said mixture comprises:
  a) a native isopentenyl diphosphate gene;
  b) a first population of nucleotide fragments which will hybridize to said native isopentenyl diphosphate gene;
  c) a second population of nucleotide fragments which will not hybridize to said native isopentenyl diphosphate gene;

wherein a mixture of restriction fragments are produced;

(ii) denaturing said mixture of restriction fragments;

(iii) incubating the denatured said mixture of restriction fragments of step (ii) with a polymerase;

(iv) repeating steps (ii) and (iii) wherein a mutated isopentenyl diphosphate gene is produced encoding a protein having an altered biological activity.

BRIEF DESCRIPTION OF THE DRAWINGS AND SEQUENCE DESCRIPTIONS

Figure 1:
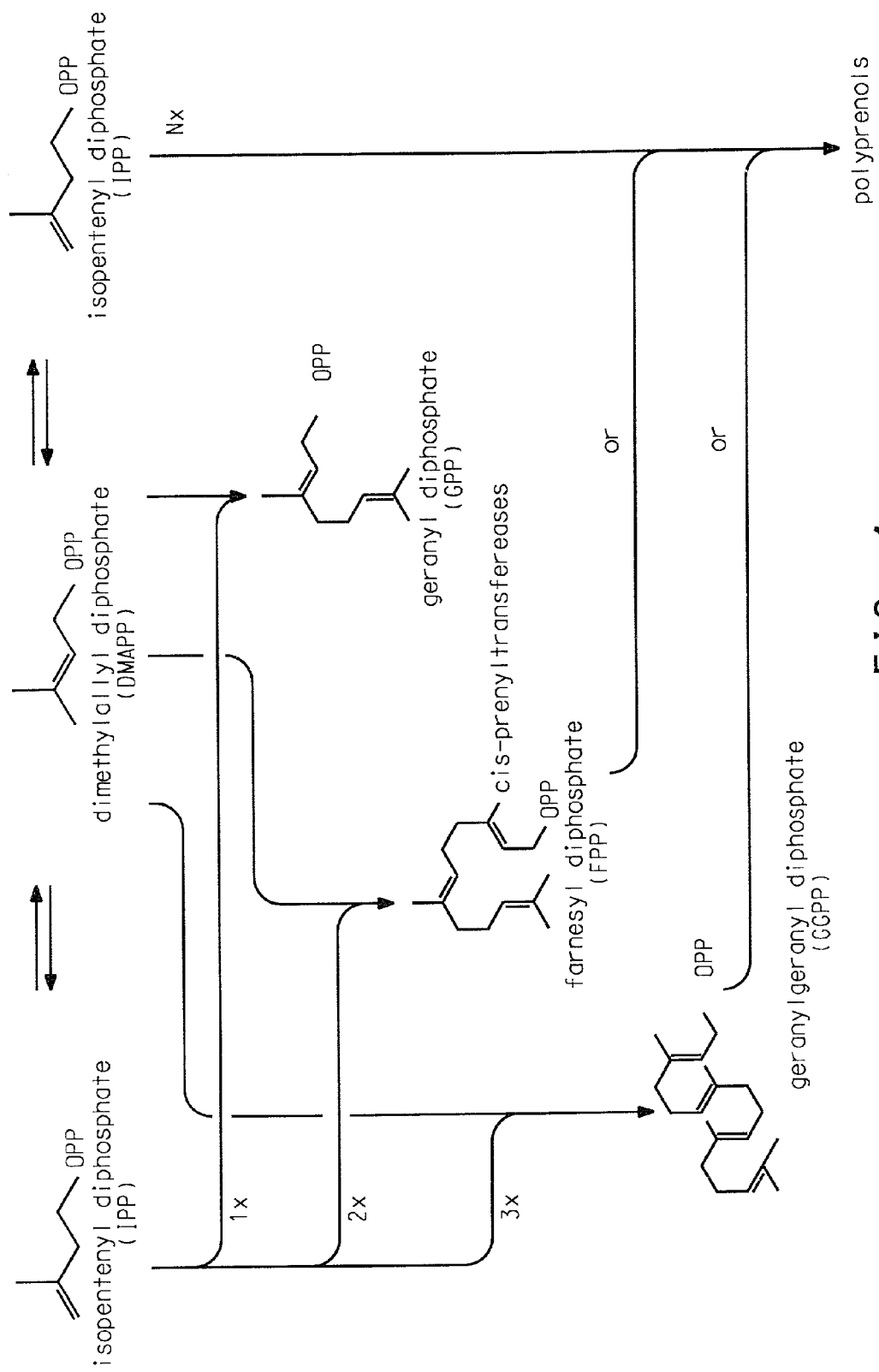
FIG. 1 illustrates the pathway of polyprenol (rubber) biosynthesis.
Figure 2:
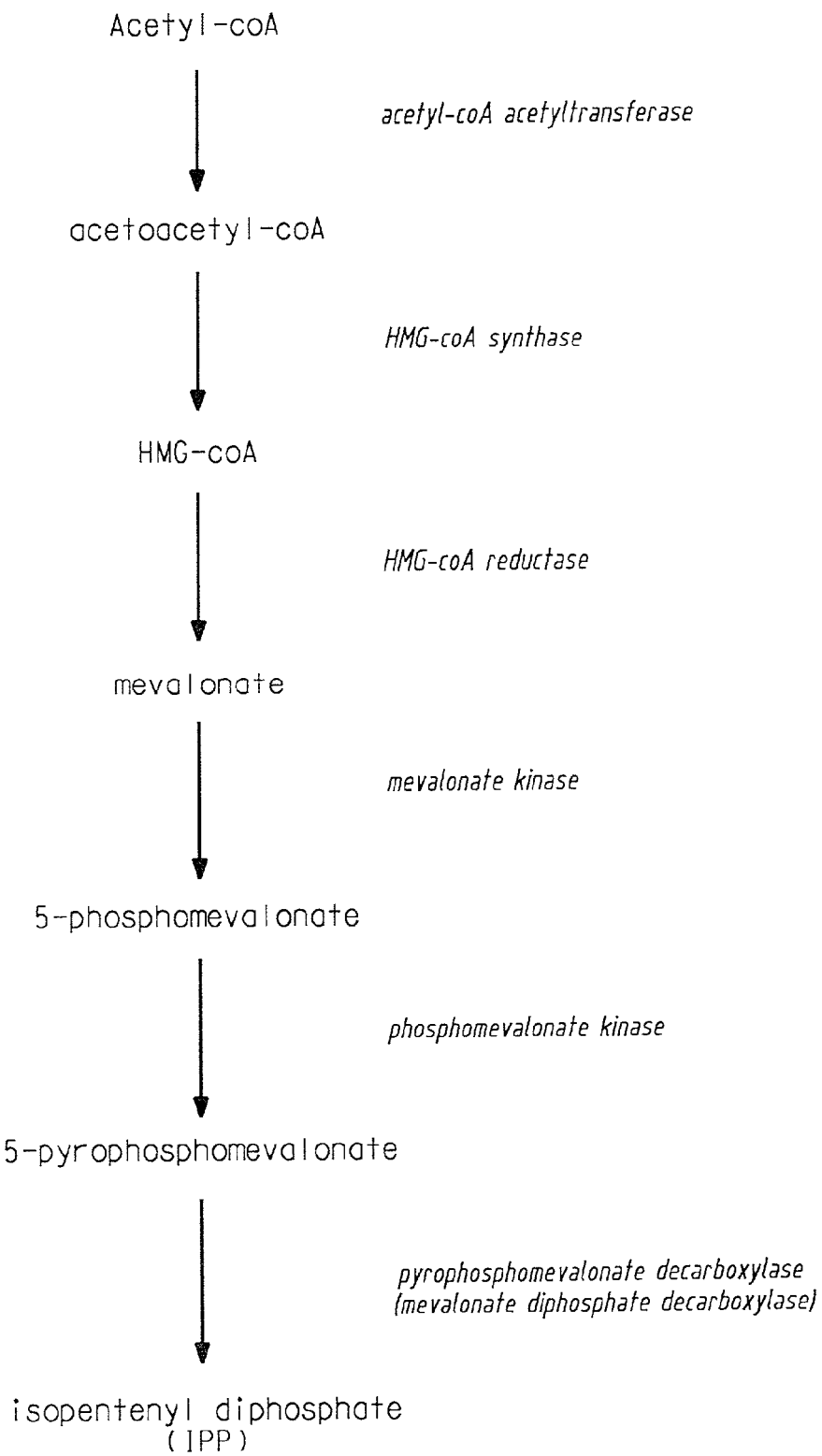
FIG. 2 illustrates the biosynthesis of IPP from acetate.

The invention can be more fully understood from the following detailed description and the accompanying sequence descriptions which form a part of this application.

The following sequence descriptions and sequences listings attached hereto comply with the rules governing nucleotide and/or amino acid sequence disclosures in patent applications as set forth in 37 C.F.R. §1.821–1.825 ("Requirements for Patent Applications Containing Nucleotide Sequences and/or Amino Acid Sequence Disclosures—The Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Adminstrative Instructions). The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

SEQ ID NO:1 is the nucleotide sequence of EST ehb2c.pk006.o5 encoding an acetyl-coA acetyltransferase enzyme isolated from a cDNA library prepared from *Hevea brasiliensis* latex.

SEQ ID NO:2 is the nucleotide sequence of EST ehb2c.pk015.b7 encoding a HMG-coA synthase enzyme isolated from a cDNA library prepared from *Hevea brasiliensis* latex.

SEQ ID NO:3 is the nucleotide sequence of EST ehb2c.pk002.d19 encoding a HMG-coA reductase enzyme isolated from a cDNA library prepared from *Hevea brasiliensis* latex.

SEQ ID NO:4 is the nucleotide sequence of EST ehb2c.pk009.d2 encoding a mevalonate kinase enzyme isolated from a cDNA library prepared from *Hevea brasiliensis* latex.

SEQ ID NO:5 is the nucleotide sequence of EST ehb2c.pk005.i13 encoding a phosphomevalonate kinase enzyme isolated from a cDNA library prepared from *Hevea brasiliensis* latex.

SEQ ID NO:6 is the nucleotide sequence of EST ehb1c.pk001.b9 encoding a mevalonate diphosphate decarboxylase enzyme isolated from a cDNA library prepared from *Hevea brasiliensis* latex.

SEQ ID NO:7 is the nucleotide sequence of EST ehb2c.pk003.i22 encoding a short homolog of an acetyl-coA acetyltransferase enzyme isolated from a cDNA library prepared from *Hevea brasiliensis* latex.

SEQ ID NO:8 is the deduced amino acid sequence of EST ehb2c.pk006.o5 encoding an acetyl-coA acetyltransferase enzyme isolated from a cDNA library prepared from *Hevea brasiliensis* latex.

SEQ ID NO:9 is the deduced amino acid sequence of EST ehb2c. pk015.b7 encoding a HMG-coA synthase enzyme isolated from a cDNA library prepared from *Hevea brasiliensis* latex.

SEQ ID NO:10 is the deduced amino acid sequence of EST ehb2c. pk002.d19 encoding a HMG-coA reductase enzyme isolated from a cDNA library prepared from *Hevea brasiliensis* latex.

SEQ ID NO:11 is the deduced amino acid sequence of EST ehb2c. pk009.d2 encoding a mevalonate kinase enzyme isolated from a cDNA library prepared from *Hevea brasiliensis* latex.

SEQ ID NO:12 is the deduced amino acid sequence of EST ehb2c. pk005.i13 encoding a phosphomevalonate kinase enzyme isolated from a cDNA library prepared from *Hevea brasiliensis* latex.

SEQ ID NO:13 is the deduced amino acid sequence of EST ehb2c. pk001.b9 encoding a mevalonate diphosphate decarboxylase enzyme isolated from a cDNA library prepared from *Hevea brasiliensis* latex.

SEQ ID NO:14 is the deduced amino acid sequence of EST ehb2c. pk003.i22 encoding a short homolog of an acetyl-coA acetyltransferase enzyme isolated from a cDNA library prepared from *Hevea brasiliensis* latex.

SEQ ID NO:15 is the Kan-2 forward primer.
SEQ ID NO:16 is the Kan-2 reverse primer.

DETAILED DESCRIPTION OF THE INVENTION

The instant invention provides the sequences encoding all enzymes in the synthesis of isopentenyl diphosphate (IPP) in latex of *Hevea brasiliensis*. More specifically, this invention pertains to the identification and characterization of EST sequences from *Hevea brasiliensis* latex encoding acetyl-coA acetyltransferase, HMG-coA synthase, mevalonate kinase, phosphomevalonate kinase and mevalonate diphosphate decarboxylase. A shorter variant of putative acetyl co-A acetyltransferase has also been identified.

The genes and their expression products are useful for the creation of recombinant organisms that have the ability to produce IPP or altered levels of IPP relative to untransformed organisms, and for the identification of new homologous genes of the acetate/mevalonate pathway having the ability, in concert, to produce isopentenyl diphosphate, or individually to alter the levels of IPP production in a recombinant organism. The importance of IPP lies in its key role in the biosynthesis of isoprenoids in living organisms. These compounds play vital roles in cell structure, electron transport, protein modification and intercellular signalling, as well as in many cases mediating interactions between organisms. Isoprenoids also comprise the largest known family of structures produced by living organisms, and the class includes mono-, sesqui- and diterpenes, sterols, carotenoids, ubiquinones, polyprenols, dolichols and rubbers. Many of these compounds are of commercial importance (i.e., monoterpenoid flavor and fragrance compounds in plant essential oils and rubbers extracted from plant latexes). Thus, bioengineering of isoprenoid (and consequently, IPP) production is likely to be of commercial value.

Full length sequences for seven ESTs from latex of *Hevea brasiliensis* have been obtained and identified by comparison to public databases containing nucleotide and protein sequences using the BLAST algorithms well known to those skilled in the art. The relevant ESTs encode complete open reading frames of each of the enzymes of the acetate/mevalonate pathway leading to IPP synthesis in *Hevea brasiliensis* and other organisms.

In this disclosure, a number of terms and abbreviations are used. The following definitions are provided.

"Acetyl-coA" is the abbreviation for acetyl-coenzymeA.

"HMG-coA" is the abbreviation for hydroxymethylglutaryl coenzyme A.

"MVA" is the abbreviation for mevalonic acid (also known as 3,5-dihydroxy-3-methylvaleric acid).

"5-Phosphomevalonate" is the abbreviation for 5-phosphate, 3,5-dihydroxy-3-methylvaleric acid.

"5-Pyrophosphomevalonate" is the abbreviation for 5-pyrophosphate, 3,5-dihydroxy-3-methylvaleric acid.

"IPP" is the abbreviation for isopentenyl diphosphate (also known as 3-methyl, 3-buten-1-ol pyrophosphate).

"DMAPP" is the abbreviation for dimethylallyl diphosphate.

"GPP" is the abbreviation for geranyl diphosphate.

"FPP" is the abbreviation for farnesyl diphosphate.

"GGPP" is the abbreviation for geranylgeranyl diphosphate.

"EST" is the abbreviation for expressed sequence tag.

"ORF" is the abbreviation for open reading frame.

"PCR" is the abbreviation for polymerase chain reaction.

As used herein, an "isopentenyl diphosphate enzyme" "isopentenyl diphosphate biosynthesis enzyme" or "isopentenyl diphosphate pathway enzyme" refers to an enzyme in the acetate/mevalonate pathway which is required to make isopentenyl diphosphate. The terms "isopentenyl diphosphate gene" "isopentenyl diphosphate biosynthesis gene" or "isopentenyl diphosphate pathway gene" refer to the genes corresponding with enzymes of isopentenyl diphosphate biosynthesis. The term "carbon substrate" or "carbon source" means any carbon source capable of being metabolized by a microorganism wherein the substrate contains at least one carbon atom, and particularly carbon sources selected from the group consisting of monosaccharides, oligosaccharides, polysaccharides, and one-carbon substrates or mixtures thereof.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein (entirely incorporated herein by reference; hereinafter "Maniatis". The conditions of temperature and ionic strength determine the "stringency" of the hybridization.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides).

Stringent conditions may also be achieved with the addition of destabilizing agents such as formamide. Exemplary low stringency conditions include hybridization with a buffer solution of 6×SSC (1 M NaCl), 30 to 35% formamide, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 6×SSC (1 M NaCl), 40 to 45% formamide, 1% SDS at 37° C., and a wash in 0.5× to 1×SSC at 55 to 60° C. Exemplary high stringency conditions include hybridization in 6×SSC (1 M NaCl), 50% formamide, 1% SDS at 37° C., and a wash in 0.1×SSC at 60 to 65° C. Alternatively, stringent conditions may also be achieved at 0.1×SSC, 0.1% SDS, 65° C. and washed with 2×SSC, 0.1% SDS followed by 0.1×SSC, 0.1% SDS.

Specificity is typically the function of post-hybridization washes, the critical factors being the ionic strength and temperature of the final wash solution. The melting temperature ($T_m$) of a probe-target hybrid can be calculated to provide a starting point for the determination of correct stringency conditions. For DNA-DNA hybrids, the $T_m$ can be approximated from the equation of Meinkoth and Wahl, *Anal. Biochem.*, 138:267–284 (1984): $T_m$=81.5° C.+16.6 (log M)+0.41 (% G+C)−0.61 (% form)−500/L; where M is the molarity of monovalent cations, % G+C is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel, et al., Eds., Greene Publishing and Wiley-Interscience, New York (1995).

A "portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403–410 (1993); ). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "portion" of a nucleotide sequence comprises enough of the sequence to specifically identify and/or isolate a nucleic acid fragment comprising the sequence. The instant specification teaches partial or complete amino acid and nucleotide sequences encoding one or more particular fungal proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., Ed.) Oxford University Press, New York (1988); *Biocomputing: Informatics and Genome Projects* (Smith, D. W., Ed.) Academic Press, New York (1993); *Computer Analysis of Sequence Data, Part I* (Griffin, A. M., and Griffin, H. G., Eds.) Humana Press, New Jersey (1994); *Sequence Analysis in Molecular Biology* (von Heinje, G., Ed.) Academic Press (1987); and *Sequence Analysis Primer* (Gribskov, M. and Devereux, J., Eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the ALIGNX program of the Vector NTI bioinformatics computing suite (InforMax Inc., Bethesda, Md.). Multiple alignment of the sequences was performed using the Clustal method of alignment (Higgins and Sharp (1989) *CABIOS.* 5:151–153) with the default parameters (GAP OPENING PENALTY=10, GAP EXTENSION PENALTY=0.05, GAP SEPARATION PENALTY RANGE=8). Default parameters for pairwise alignments using the Clustal method were KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), the Vector NTI bioinformatics computing suite (InforMax Inc., Bethesda, Md.) and the FASTA program incorporating the Smith-Waterman algorithm (W. R. Pearson, *Comput. Methods Genome Res., [Proc. Int. Symp.]* (1994), Meeting Date 1992, 111-20. Editor(s): Suhai, Sandor. Publisher: Plenum, New York,). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the *Hevea brasiliensis* acetate/mevalonate pathway enzymes as set forth in SEQ ID NO:8, SEQ ID NO:9, SEQ ID NO:11, SEQ ID NO:12, SEQ ID NO:13 and SEQ ID NO:14.

The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to an RNA transcript that is complementary to all or part of a target primary transcript or mRNA that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

Standard recombinant DNA and molecular cloning techniques used here are well known in the art as described by Sambrook, J., Fritsch, E. F. and Maniatis, T., Molecular Cloning: A Laboratory Manual, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., Experiments with Gene Fusions, Cold Spring Harbor Laboratory Cold Press Spring Harbor, N.Y. (1984); and by Ausubel, F. M. et al., Current Protocols in Molecular Biology, published by Greene Publishing Assoc. and Wiley-Interscience (1987).

The invention provides new sequences encoding enzymes for the synthesis of IPP from acetate. These sequences comprising five open reading frames within cDNAs isolated from *Hevea brasiliensis*, all encode identifiable enzymes known to be useful in the synthesis of IPP. The present genes were identified on the basis of comparison of the nucleic acid and deduced amino acid sequences to public databases using algorithms well known in the art. Specifically EST's encoding an acetyl-coA acetyltransferase enzyme (SEQ ID NO:1, SEQ ID NO:7); a HMG-coA synthase enzyme (SEQ ID NO:2); a HMG-coA reductase enzyme (SEQ ID NO:3); a mevalonate kinase enzyme (SEQ ID NO:4); a phosphomevalonate kinase enzyme (SEQ ID NO:5); a mevalonate diphosphate decarboxylase enzyme (SEQ ID NO:6).

Comparison of the acetyl-coA acetyltransferase enzyme nucleotide base and deduced amino acid sequences to public databases reveals that the most similar known sequences is about 65% identical to the amino acid sequence reported herein (SEQ ID NO:8) over length of 411 amino acids using a CLUSTALW alignment algorithm (Vector NTI suite—InforMax Inc., Bethesda, Md.). More preferred amino acid fragments are at least about 80%–90% identical to the sequences herein. Most preferred are nucleic acid fragments that are at least 95% identical to the amino acid fragments reported herein. Similarly, preferred acetyl-coA acetyltransferase encoding nucleic acid sequences corresponding to the instant EST's are those encoding active proteins and which are at least 80% identical to the nucleic acid sequences of reported herein. More preferred acetyl-coA acetyltransferase nucleic acid fragments are at least 90% identical to the sequences herein. Most preferred are acetyl-coA acetyltransferase nucleic acid fragments that are at least 95% identical to the nucleic acid fragments reported herein.

Comparison of the HMG-coA synthase enzyme nucleotide base and deduced amino acid sequences to public databases reveals that the most similar known sequences is about 82% identical to the amino acid sequence reported herein (SEQ ID NO:9) over length of 464 amino acids using a CLUSTALW alignment algorithm (Vector NTI suite—InforMax Inc., Bethesda, Md.). More preferred amino acid fragments are at least about 80%–90% identical to the sequences herein. Most preferred are nucleic acid fragments that are at least 95% identical to the amino acid fragments reported herein. Similarly, preferred are HMG-coA synthase enzyme encoding nucleic acid sequences corresponding to the instant EST's are those encoding active proteins and which are at least 80% identical to the nucleic acid sequences of reported herein. More preferred a HMG-coA synthase enzyme nucleic acid fragments are at least 90% identical to the sequences herein. Most preferred are HMG-coA synthase enzyme nucleic acid fragments that are at least 95% identical to the nucleic acid fragments reported herein.

Comparison of the mevalonate kinase enzyme nucleotide base and deduced amino acid sequences to public databases reveals that the most similar known sequences is about 68% identical to the amino acid sequence reported herein (SEQ ID NO:11) over length of 386 amino acids using a CLUSTALW alignment algorithm (Vector NTI suite—InforMax Inc., Bethesda, Md.). More preferred amino acid fragments are at least about 80%–90% identical to the sequences herein. Most preferred are nucleic acid fragments that are at least 95% identical to the amino acid fragments reported herein. Similarly, preferred are mevalonate kinase enzyme encoding nucleic acid sequences corresponding to the instant EST's are those encoding active proteins and which are at least 80% identical to the nucleic acid sequences of reported herein. More preferred are mevalonate kinase enzyme nucleic acid fragments are at least 90% identical to the sequences herein. Most preferred are mevalonate kinase enzyme nucleic acid fragments that are at least 95% identical to the nucleic acid fragments reported herein.

Comparison of the phosphomevalonate kinase enzyme nucleotide base and deduced amino acid sequences to public databases reveals that the most similar known sequences is about 73% identical to the amino acid sequence reported herein (SEQ ID NO:12) over length of 503 amino acids using a CLUSTALW alignment algorithm (Vector NTI suite—InforMax Inc., Bethesda, Md.). More preferred amino acid fragments are at least about 80%–90% identical to the sequences herein. Most preferred are nucleic acid fragments that are at least 95% identical to the amino acid fragments reported herein. Similarly, preferred are phosphomevalonate kinase enzyme encoding nucleic acid sequences corresponding to the instant EST's are those encoding active proteins and which are at least 80% identical to the nucleic acid sequences of reported herein. More preferred are phosphomevalonate kinase enzyme nucleic acid fragments are at least 90% identical to the sequences herein. Most preferred are phosphomevalonate kinase enzyme nucleic acid fragments that are at least 95% identical to the nucleic acid fragments reported herein.

Comparison of the mevalonate diphosphate decarboxylase enzyme nucleotide base and deduced amino acid sequences to public databases reveals that the most similar known sequences is about 77% identical to the amino acid sequence reported herein (SEQ ID NO:13) over length of 415 amino acids using a CLUSTALW alignment algorithm (Vector NTI suite—InforMax Inc., Bethesda, Md.). More preferred amino acid fragments are at least about 80%–90% identical to the sequences herein. Most preferred are nucleic acid fragments that are at least 95% identical to the amino acid fragments reported herein. Similarly, preferred are mevalonate diphosphate decarboxylase enzyme encoding nucleic acid sequences corresponding to the instant EST's are those encoding active proteins and which are at least 80% identical to the nucleic acid sequences of reported herein. More preferred are mevalonate diphosphate decarboxylase enzyme nucleic acid fragments are at least 90% identical to the sequences herein. Most preferred are mevalonate diphosphate decarboxylase enzyme nucleic acid fragments that are at least 95% identical to the nucleic acid fragments reported herein.

Isolation of Homologs

The nucleic acid fragments of the instant invention may be used to isolate cDNAs and genes encoding homologous enzymes from the same or other species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding similar enzymes to those of the instant acetate/mevalonate pathway, either as cDNAs or genomic DNAs, could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

Where PCR is employed, two short segments of the instant SEQ ID NOs:1, 2, 4, 5 and 6 may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor. Alternatively, the second primer sequence may be based upon sequences derived from the cloning vector. For example, the skilled artisan can follow the RACE protocol (Frohman et al., PNAS USA 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., PNAS USA 86:5673 (1989); Loh et al., Science 243:217 (1989)).

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The Use of Oligonucleotide as Specific Hybridization Probes in the Diagnosis of Genetic Disorders", in *Human Genetic Diseases: A Practical Approach*, K. E. Davis Ed., (1986) pp. 33–50 IRL Press, Herndon, Va.); Rychlik, W. (1993) In White, B. A. (Ed.), *Methods in Molecular Biology*, Vol. 15, pages 31–39, PCR Protocols: Current Methods and Applications. Humania Press, Inc., Totowa, N.J.)

Alternatively the instant sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Only part of the probe molecule need be complementary to the nucleic acid sequence to be detected. In addition, the complementarily between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143–5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kilodaltons), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Plant Expression

The nucleic acid fragments of the present invention may also be used to create transgenic plants in which the present isopentenyl diphosphate pathway enzyme is present at higher or lower levels than normal. Alternatively, in some applications, it might be desirable to express the present isopentenyl diphosphate pathway enzyme in specific plant tissues and/or cell types, or during developmental stages in which they would normally not be encountered. The expression of full-length plant isopentenyl diphosphate pathway cDNAs (ie., any of the present sequences or related sequences incorporating an appropriate in-frame ATG start codon) in a bacterial (e.g., *E. coli*), yeast (e.g., *Saccharomyces cerevisiae, Pichia pastoralis*) or plant yields a mature protein capable of participating in isopentenyl diphosphate biosynthesis.

It is contemplated that transgenic plants expressing the present isopentenyl diphosphate pathway sequences will have altered or modulated defense mechanisms against various pathogens and natural predators. For example, various latex proteins are known to be antigenic and recognized by IgE antibodies, suggesting their role in immunolgical defense (Yagami et al., *Journal of Allergy and Clinical Immunology,* (March, 1998) Vol. 101, No. 3, pp. 379–385. Additionally, it has been shown that a significant portion of the latex isolated from *Hevea brasiliensis* contains chitinases/lysozymes, which are capable of degrading the chitin component of fungal cell walls and the peptidoglycan component of bacterial cell walls (Martin, M. N., *Plant Physiol* (Bethesda), 95(2):469–476 (1991)). It is therefore an object of the present invention to provide transgenic plants having altered, modulated or increased defenses towards various pathogens and herbivores.

The plant species suitable for expression of the present sequences may be (but are not limited to) rubber tree (*Hevea brasiliensis*), tobacco (*Sicotiana* spp.), tomato (Lycopersicon spp.), potato (*Solanum* spp.), hemp (Cannabis spp.), sunflower (*Helianthus* spp.), sorghum (*Sorghum vulgare*), wheat (*Triticum* spp.), maize (*Zea mays*), rice (*Oryza sativa*), rye (*Secale cereale*), oats (*Avena* spp.), barley (*Hordeum vulgare*), rapeseed (*Brassica* spp.), broad bean (*Vicia faba*), french bean (*Phaseolus vulgaris*), other bean species (*Vigna* spp.), lentil (*Lens culinaris*), soybean (*Glycine max*), arabidopsis (*Arabidopsis thaliana*), guayule (*Parthenium argentatum*), cotton (*Gossypium hirsutum*), petunia (*Petunia hybrida*), flax (*Linum usitatissimum*) and carrot (*Daucus carota sativa*).

Overexpression of the present isopentenyl diphosphate pathway homologs may be accomplished by first constructing a chimeric gene in which their coding region is operably-linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals must also be provided. The present chimeric genes may also comprise one or more introns in order to facilitate gene expression.

Plasmid vectors comprising the present chimeric genes can then be constructed. The choice of a plasmid vector depends upon the method that will be used to transform host plants. The skilled artisan is well aware of the genetic elements that must be present on the plasmid vector in order to successfully transform, select and propagate host cells containing the chimeric gene. For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of a isopentenyl diphosphate pathway gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, and the GRP1–8 promoter.

Alternatively, the plant promoter can direct expression of the isopentenyl diphosphate pathway gene in a specific tissue or may be otherwise under more precise environmental or developmental control. Such protmoter are referred to here as "inducible" promoters. Environmental conditions that may effect transcription by inducible promoters include pathogen attack, anaerobic conditions, or the presence of light. Examples of inducible promoters are the Adh1 promoter which is inducible by hypoxia or cold stress, the Hsp70 promoter which is inducible by heat stress, and the PPDK promoter which is inducible by light.

Examples of promoters under developmental control include promoters that initiate transcription only, or preferentially, in certain tissues, such as leaves, roots, fruit, seeds, or flowers. Exemplary promoters include the anther specific promoter 5126 (U.S. Pat. Nos. 5,689,049 and 5,689,051), glob-1 promoter, and gamma-zein promoter. The operation of a promoter may also vary depending on its location in the genome. Thus, an inducible promoter may become fully or partially constitutive in certain locations.

Both heterologous and non-heterologous (i.e., endogenous) promoters can be employed to direct expression of isopentenyl diphosphate pathway gene. These promoters can also be used, for example, in recombinant expression cassettes to drive expression of antisense nucleic acids to reduce, increase, or alter concentration and/or composition of the isopentenyl diphosphate pathway protein in a desired tissue. Thus, in some embodiments, the nucleic acid construct will comprise a promoter functional in a plant cell, such as in *Zea mays* or tobacco, operably linked to an isopentenyl diphosphate pathway biosynthetic gene. Gene promoters useful in these embodiments include the endogenous promoters driving expression of the isopentenyl diphosphate pathway proteins.

In some embodiments, isolated nucleic acids which serve as promoter or enhancer elements can be introduced in the appropriate position (generally upstream) of a non-heterologous form of the isopentenyl diphosphate pathway polynucleotides so as to up or down regulate its expression. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from the isopentenyl diphosphate pathway genes so as to control the expression of the gene. Expression of the isopentenyl diphosphate pathway genes can be modulated under conditions suitable for plant growth so as to alter the total concentration and/or alter the composition of isopentenyl diphosphate pathway proteins in a plant cell. Thus, the present invention provides compositions, and methods for making, heterologous promoters and/or enhancers operably linked to a native, endogenous (i.e., non-heterologous) form of isopentenyl diphosphate pathway proteins.

Where isopentenyl diphosphate pathway polypeptide expression is desired, it is generally desirable to include a polyadenylation region at the 3'-end of a polynucleotide coding region of the isopentenyl diphosphate pathway genes. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8:4395–4405 (1988); Callis et al., *Genes Dev.* 1:1183–1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, New York (1994). The vector comprising the isopentenyl diphosphate pathway sequence will typically comprise a marker gene which confers a selectable phenotype on plant cells. Typical vectors useful for expression of genes in higher plants are well known in the art and include vectors derived from the tumor-inducing (Ti) plasmid of *Agrobacterium tumefaciens* described by Rogers et al., *Meth. Enzymol.* 153:253–277 (1987).

Optionally, the isopentenyl diphosphate pathway gene may introduced into a plant. Generally, the gene will first be incorporated into a recombinant expression cassette or vector, by a variety of methods known in the art. See, for example, Weising et al., *Ann. Rev. Genet.* 22:421–477 (1988). For example, the DNA construct may be introduced directly into the genomic DNA of the plant cell using techniques such as electroporation, polyethylene glycol (PEG), poration, particle bombardment, silicon fiber delivery, or microinjection of plant cell protoplasts or embryogenic callus. See, e.g., Tomes et al., Direct DNA Transfer into Intact Plant Cells via Microprojectile Bombardment, pp.197–213 in *Plant Cell, Tissue and Organ Culture, Fundamental Methods*, Eds. O. L. Gamborg and G. C. Phillips, Springer-Verlag Berlin Heidelberg, New York (1995). The introduction of DNA constructs using PEG precipitation is described in Paszkowski et al., *Embo J.* 3:2717–2722 (1984). Electroporation techniques are described in Fromm et al., *Proc. Natl. Acad. Sci.(USA)* 82:5824 (1985). Biolistic transformation techniques are described in Klein et al., *Nature* 327:70–73 (1987). For example, biolistic transformation of *Hevea brasiliensis* is described in U.S. Pat. No. 5,580,768.

Alternatively, *Agrobacterium tumefaciens*-mediated transformation techniques may be used. See, for example Horsch et al., *Science* 233:496–498 (1984); Fraley et al., *Proc. Natl. Acad. Sci.* (USA) 80:4803 (1983); and *Plant Molecular Biology: A Laboratory Manual*, Chapter 8, Clark, Ed., Springer-Verlag, Berlin (1997). The DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria (U.S. Pat. No. 5,591,616). Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (e.g., Lichtenstein and Fuller, in *Genetic Engineering, vol. 6*, P W J Rigby, Ed., London, Academic Press (1987); and Lichtenstein, C. P., and Draper, J,. in *DNA Cloning*, Vol. II, D. M. Glover, Ed., Oxford, IRI Press (1985)); Application PCT/US87/02512 (WO 88/02405 published Apr. 7, 1988) describes the use of *A. rhizogenes* strain A4 and its Ri plasmid along with *A. tumefaciens* vectors pARC8 or pARC16) (2) liposome-mediated DNA uptake (e.g., Freeman et al., *Plant Cell Physiol.* 25:1353 (1984)), (3) the vortexing method (e.g., Kindle, *Proc. Natl. Acad. Sci.*, (USA) 87:1228 (1990)).

Plant cells which directly result or are derived from the nucleic acid introduction techniques can be cultured to regenerate a whole plant which possesses the introduced genotype. Such regeneration techniques often rely on manipulation of certain phytohormones in a tissue culture growth medium. Plants cells can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmillan Publishing Company, NY, pp. 124–176 (1983); and *Binding, Regeneration of Plants, Plant Protoplasts*, CRC Press, Boca Raton, pp. 21–73 (1985).

The regeneration of plants from either single plant protoplasts or various explants is well known in the art. See, for example, *Methods for Plant Molecular Biology*, A. Weissbach and H. Weissbach, Eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook*, Freeling and Walbot, Eds., Springer, New York (1994); *Corn and Corn Improvement*, $3^{rd}$ edition, Sprague and Dudley Eds., American Society of Agronomy, Madison, Wis. (1988). For transformation and regeneration of maize see, Gordon-Kamm et al., *The Plant Cell*, 2:603–618 (1990).

The regeneration of plants containing the isopentenyl diphosphate pathway gene and introduction by Agrobacterium from leaf explants can be achieved as described by Horsch et al., *Science*, 227:1229–1231 (1985). In this procedure, transformants are grown in the presence of a selection agent and in a medium that induces the regeneration of shoots in the plant species being transformed as described by Fraley et al., *Proc. Natl. Acad. Sci.* (U.S.A.), 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype. Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing the isopentenyl diphosphate pathway gene can be screened for transmission of the nucleic acid of the present invention by, for example, standard immunoblot and DNA detection techniques. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according tostandard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

For some applications it may be useful to direct the isopentenyl diphosphate pathway enzyme to different cellular compartments or to facilitate their secretion from the cell. The chimeric genes described above may be further modified by the addition of appropriate intracellular or extracellular targeting sequence to their coding regions. These include chloroplast transit peptides (Keegstra et al., *Cell* 56:247–253 (1989)), signal sequences that direct proteins to the endoplasmic reticulum (Chrispeels et al., *Ann. Rev. Plant Phys. Plant Mol.* 42:21–53 (1991)), and nuclear localization signal (Raikhel et al., *Plant Phys.* 100:1627–1632 (1992)). While the references cited give examples of each of these, the list is not exhaustive and more targeting signals of utility may be discovered in the future.

It may also be desirable to reduce or eliminate expression of the isopentenyl diphosphate pathway genes in plants for some applications. In order to accomplish this, chimeric genes designed for antisense or co-suppression of isopentenyl diphosphate pathway homologs can be constructed by linking the genes or gene fragments encoding parts of these enzymes to plant promoter sequences. Thus, chimeric genes designed to express antisense RNA for all or part of a UPPS homolog can be constructed by linking the isopentenyl diphosphate pathway homolog genes or gene fragments in reverse orientation to plant promoter sequences. The co-suppression or antisense chimeric gene constructs could be introduced into plants via well known transformation protocols wherein expression of the corresponding endogenous genes are reduced or eliminated.

Microbial Expression

The present isopentenyl diphosphate pathway homolog proteins may be produced in heterologous host cells, particularly in the cells of microbial hosts, and can be used to prepare antibodies to the proteins by methods well known to those skilled in the art. The antibodies would be useful for detecting the present isopentenyl diphosphate pathway enzyme in situ in cells or in vitro in cell extracts. Preferred heterologous host cells for production of the present isopentenyl diphosphate pathway enzymes are microbial hosts. Microbial expression systems and expression vectors containing regulatory sequences that direct high level expression of foreign proteins are well known to those skilled in the art. Any of these could be used to construct a chimeric gene for production of the present isopentenyl diphosphate pathway homologs. This chimeric gene could then be introduced into appropriate microorganisms via transformation to provide high level expression of the present isopentenyl diphosphate pathway enzymes. Specific suitable hosts include but are not limited to yeasts such as *Aspergillus, Trichoderma, Saccharomyces, Pichia, Candida, Hansenula*, or bacterial species such as *Salmonella, Bacillus, Acinetobacter, Zymomonas, Agrobacterium, Flavobacterium, Rhodobacter, Rhodococcus, Streptomyces, Brevibacterium, Corynebacteria, Mycobacterium, Escherichia, Erwinia, Pseudomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium* and *Klebsiella*.

Microbial expression systems and expression vectors containing regulatory sequences that direct high level expression of foreign proteins are well known to those skilled in the art. Any of these could be used to construct chimeric genes for production of any of the gene products of the nucleic acid fragments reported herein. These chimeric genes could then be introduced into appropriate microorganisms via transformation to provide high level expression of the enzymes.

Additionally, chimeric genes will be effective in altering the properties of a host plant. It is expected, for example, that introduction of chimeric genes encoding one or more of the instant sequences described herein under the control of the appropriate promoters, into a host cell comprising at least one copy of these genes will demonstrate the ability to convert one or more of the precursors of IPP to the appropriate enzymatic products. Additionally expression of such sequences, either separately or together may facilitate the mediation of acetate to IPP, or any of the intermediate steps depending on the presence or absence of these proteins in the host.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant sequences in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); lac, trp, $IP_L$, $IP_R$, T7, tac, and trc (useful for expression in *Escherichia coli*) and CaMV 35S (useful for expression in plants).

Termination control regions may also be derived from various genes native to the preferred hosts. Optionally, a termination site may be unnecessary however; it is most preferred if included.

Isopentenyl Diphosphate Pathway Genes Having Enhanced Activity

It is contemplated that the present nucleotides may be used to produce gene products having enhanced or altered activity. Various methods are known for mutating a native gene sequence to produce a gene product with altered or enhanced activity including but not limited to error prone PCR (Melnikov et al., *Nucleic Acids Research*, (Feb. 15, 1999) Vol. 27, No. 4, pp. 1056–1062); site directed mutagenesis (Coombs et al., *Proteins* (1998), 259–311, 1 plate. Editor(s): Angeletti, Ruth Hogue. Publisher: Academic, San Diego, Calif.) and "gene shuffling" (U.S. Pat. Nos. 5,605, 793; 5,811,238; 5,830,721; and 5,837,458, incorporated herein by reference).

The method of gene shuffling is particularly attractive due to its facile implementation, and high rate of mutagenesis and ease of screening. The process of gene shuffling involves the restriction of a gene of interest into fragments of specific size in the presence of additional populations of DNA regions of both similarity to or difference to the gene of interest. This pool of fragments was then denatured and then reannealed to create a mutated gene. The mutated gene is then screened for altered activity.

The instant plant sequences may be mutated and screened for altered or enhanced activity by this method. The sequences may be randomly digested into fragments ranging from about 10 bp to 1000 bp, using restriction endonucleases well known in the art (Maniatis). In addition to the instant sequences populations of fragments that are hybridizable to all or portions of the sequence may added. Similarly, a population of fragments which are not hybridizable to the instant sequence may also be added. Typically these additional fragment populations are added in about 10 to 20 fold excess by weight as compared to the total nucleic acid. Generally if this process is followed the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double stranded nucleic acid. Preferably the temperature is from 80° C. to 100° C. Nucleic acid fragments may be reannealed by cooling. Preferably the temperature is from 20° C. to 75° C. Renaturation can be accelerated by the addition of polyethylene glycol ("PEG") or salt. The salt concentration is preferably from 0 mM to 200 mM. The annealed nucleic acid fragments are next incubated in the presence of a nucleic acid polymerase and dNTP's (i.e. dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from 2 to 50 times, more preferably the sequence is repeated from 10 to 40 times. The resulting nucleic acid is a larger double-stranded polynucleotide of from about 50 bp to about 100 kb and may be screened for expression and altered activity by standard cloning and expression protocol (Maniatis, supra).

DESCRIPTION OF THE PREFERRED EMBODIMENTS

The present invention relates to the isolation of genes encoding enzymes useful for the conversion of acetate to IPP. The relevant genes were isolated from latex tapped from the tree species *Hevea brasiliensis*, by isolating messenger RNA and synthesizing complementary DNA (cDNA). The cDNA was used to construct a gene library by standard methods, which in turn was randomly sampled for sequence analysis.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., Current Protocols in Molecular Biology, published by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds.), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989).

Manipulations of genetic sequences were accomplished using the BLAST family of programs which can be used for database similarity searches. The family includes BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995). Software for performing BLAST analyses is publicly available, e.g., through the National Center for Biotechnology Information and other sources (BLAST Manual, Altschul et al., Natl. Cent. Biotechnol. Inf., Natl. Library Med. (NCBI NLM) NIH, Bethesda, Md. 20894; Altschul et al., *J. Mol. Biol.* 215:403–410 (1990)).

Example 1

Composition of cDNA Libraries Used for Identification of cDNA Clones from *Hevea brasiliensis* Latex cDNA libraries representing mRNAs from rubber tree latex collected at various stages during a tapping cycle were prepared. cDNA libraries may be prepared by any one of many methods available. For example, the cDNAs may be introduced into plasmid vectors by first preparing the cDNA libraries in Uni-ZAP XR vectors according to the manufacturer's protocol (Stratagene Cloning Systems, La Jolla, Calif.). The Uni-ZAP XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., *Science* 252: 1651–1656 (1991).

Example 2

Identification of ESTs

ESTs were identified by conducting BLAST (Basic Local Alignment Search Tool; Altschul et al., *J. Mol. Biol.* 215: 403–410 (1993) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. *Nature Genetics* 3:266–272 (1993)) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Identification of cDNA Clones for Acetate/Mevalonate Pathway Enzymes cDNAs from the libraries were identified based on interrogation of the database described in Examples 1 and 2. cDNAs were thus identified by a number of methods, including the following: 1) keyword searches 2) searches of the database using the TBLASTN algorithm provided by the National Center for Biotechnology Information (NCBI) and sequences of known acetate/mevalonate pathway genes, and 3) identification of further homologs of cDNAs discovered by 1 and 2 within the in-house database using the FASTA program. The cDNAs identified by these means are listed in Table 1.

TABLE 1

Initial Identification of Hevea Latex ESTs as Acetate/Mevalonate Pathway Enzymes Using BLAST Searches of Public Databases

| Acetate/<br>Mevalonate<br>Pathway Enzyme | Public Database Homolog<br>(protein id) | H. brasiliensis<br>homolog | pLog<br>(Xnr) |
|---|---|---|---|
| acetyl-coA acetyltransferase | A. thaliana AB023039 (BAA97003) | ehb2c.pk006.o5 | 4.70 |
| HMG-coA synthase | B. juncea AF188639 (AAG32922) | ehb2c.pk015.b7 | 22.21 |
| HMG-coA reductase | H. brasiliensis X54659 (P29057) | ehb2c.pk002.d19 | 32.09 |
| mevalonate kinase | A. thaliana X77793 (P46086) | ehb2c.pk009.d2 | 17.21 |
| phospho-mevalonate kinase | A. thaliana AC079041.4 (AAG50716.1) | ehb2c.pk005.i13 | 16.08 |
| mevalonate diphosphate decarboxylase | A. thaliana Y14325 (CAA74700) | ehb1c.pk001.b9 | 15.96 |

Example 4

Full-Length Sequencing of ESTs and Verification of Identity

EST's assigned a putative identification were fully sequenced to confirm their identity. Plasmid DNAs containing the ESTs in the vector pBluescript SK+ (Stratagene, La Jolla, Calif.), were prepared using a Qiagen miniprep kit (Qiagen, Inc., Valencia), according to manufacturer's instructions. A transposon containing primer binding sites and a kanamycin resistance selection marker was randomly inserted into each of the plasmids containing the target EST's for full length sequencing, using the EZ:TN<Kan-2> Insertion Kit (Epicentre, Madison, Wis.), according to manufacturer's instructions. These plasmids were then transformed into TransforMax EC100 Electrocompetent E. coli (Epicentre, Madison, Wis.) by electroporation, using the Bio-Rad Gene Pulser II (Bio-Rad, Hercules, Calif.), at 25 uF, 1.8 KV and 200Ω. Plasmids containing the transposon insertion were selected for on LB-Agar plates containing 50 µg/mL kanamycin and 50 µg/mL ampicillin. Twenty plasmid DNA's, containing the EZ:TN<Kan-2> transposon, for each of the EST's were prepared, using the Montage Plasmid Miniprep$_{96}$ Kit (Millipore, Bedford, Mass.). Plasmids were sequenced on an ABI sequencer, using the Kan-2 Forward Primer 5' ACCTACAACAAAGCTCTCATCAACC 3' (SEQ ID NO:15) and Kan-2 Reverse Primer 5'GCAATGTAA-CATCAGAGATTTTGAG 3' (SEQ ID NO:16) which bind to the EZ:TN<Kan-2> transposon. Those sequences showing homology only to the original host vector, pBluescript SK+, were discarded. DNA sequence representing the EZ:TN transposon was removed and full length gene sequences were assembled using Vector NTI Contig Express (Informax, Inc., North Bethesda, Md.).

Alignment of the deduced amino acid sequences of the cDNAs thus identified with homologs in the public databases indicated a high degree of homology (Table 2).

TABLE 2

Alignments of the Deduced Amino Acid Sequences of ESTs Encoding Acetate/Mevalonate Pathway Genes of Hevea with Their Homologs in the Public Databases

| Acetate/Mevalonate<br>Pathway Enzyme<br>(SEQ ID NO) | Public<br>Homolog<br>(protein id. no.) | Hevea EST | % Similarity<br>(a) | % Identity<br>(b) | Citation |
|---|---|---|---|---|---|
| acetyl-coA acetyltransferase (SEQ ID NO: 8) | BAA97003 | ehb2c.pk006.05 | 73.4 | 64.5 | 1 |
| HMG-coA synthase (SEQ ID NO: 9) | AAG32922 | ehb2c.pk015.b7 | 88.8 | 82.6 | 2 |
| HMG-coA reductase (SEQ ID NO: 10) | P29057 | ehb2c.pk002.d19 | 100 | 100 | 3 |
| mevalonate kinase (SEQ ID NO: 11) | P46086 | ehb2c.pk009.d2 | 78.9 | 68.6 | 4 |
| phosphomevalonate kinase (SEQ ID NO: 12) | AAG50716.1 | ehb2c.pk005.i13 | 82.6 | 73.5 | 5 |

TABLE 2-continued

Alignments of the Deduced Amino Acid Sequences of ESTs
Encoding Acetate/Mevalonate Pathway Genes of Hevea
with Their Homologs in the Public Databases

| Acetate/Mevalonate Pathway Enzyme (SEQ ID NO) | Public Homolog (protein id. no.) | Hevea EST | % Similarity (a) | % Identity (b) | Citation |
|---|---|---|---|---|---|
| mevalonate diphosphate decarboxylase (SEQ ID NO: 13) | CAA74700 | ehb1c.pk001.b9 | 85.1 | 77.9 | 6 | a % Similarity is defined as percentage of amino acids that are identical or conserved between the two proteins.
b % Identity is defined as percentage of amino acids that are identical between the two proteins.
Citations:
1 Sato, S., Nakamura, Y., Kaneko, T., Katoh, T., Asamizu, E., Kotani, H. and Tabata, S. Structural analysis of *Arabidopsis thaliana* chromosome 5. X. Sequence features of the regions of 3,076,755 bp covered by sixty P1 and TAC clones. DNA Res. 7 (1), 31–63 (2000)
2 Alex, D., Bach, T.J. and Chye, M.L. Expression of Brassica juncea 3-hydroxy-3-methylglutaryl CoA synthase is developmentally regulated and stress-responsive. Plant J. 22 (5), 415–426 (2000)
3 Chye, M.L., Kush, A., Tan, C.T. and Chua, N.H. Characterization of cDNA and genomic clones encoding 3-hydroxy-3-methylglutaryl-coenzyme A reductase from *Hevea brasiliensis*. Plant Mol. Biol. 16 (4), 567–577 (1991)
4 Riou, C., Tourte, Y., Lacroute, F. and Karst, F. Isolation and characterization of a cDNA encoding *Arabidopsis thaliana* mevalonate kinase by genetic complementation in yeast. Gene 148 (2), 293–297 (1994)
5 Direct Submission (Aug. 17, 2000) The Institute for Genomic Research, 9712 Medical Center Dr, Rockville, MD 20850, USA
6 Cordier, H., Karst, F. and Berges, T. Heterologous expression in *Saccharomyces cerevisiae* of an *Arabidopsis thaliana* cDNA encoding mevalonate diphosphate decarboxylase. Plant Mol. Biol. 39 (5), 953–967 (1999)

Alignment for the data in Table 2 was conducted using the CLUSTALW algorithm in the software package Vector NTI, with default settings.

Based on these comparisons, it can be concluded that the EST sequences identified (Table 1) are, in *Hevea* latex, homologous to those previously described from other species. In all cases, their % identity with the known sequences is greater than 64% (Table 2). The public sequences used for comparison have all been identified, by experimentation or homology, as genes encoding enzymes of the acetate-mevalonate pathway in plants. Thus the Hevea genes identified most likely carry out the same enzymatic activities in the pathway from acetate to IPP in latex of this species. The EST sequence (SEQ ID NO:3) identified by homology as encoding an HMG-coA reductase enzyme yields a deduced amino acid sequence (SEQ ID NO:10) 100% identical to that of the known Hevea isoform HMGR1 (Table 2), and distinct from HMGR2 and HMGR3 of this organism. However, the nucleotide sequence of this EST differed from the sequence of HMGR1 by 15 bases, and in addition the 3'-noncoding region differed significantly in its possession of a poly(A) tail. Thus the EST ehb2c.pk002.d19 (SEQ ID NO:3) represents a new isoform of HMG-coA reductase present in *Hevea brasiliensis*, which we term HMGR4.

To summarize, complete and novel cDNA sequences were obtained for acetyl-coA acetyltransferase (SEQ ID NO:1), HMG-coA synthase (SEQ ID NO:2), HMG-coA reductase (SEQ ID NO:3), mevalonate kinase (SEQ ID NO:4), phosphomevalonate kinase (SEQ ID NO:5) and mevalonate diphosphate decarboxylase (SEQ ID NO:6) of *Hevea brasiliensis*. Furthermore, the DNA sequences were translated into their corresponding protein sequences SEQ ID NO:8, SEQ ID NO:9, SEQ ID NO:10, SEQ ID NO:11, SEQ ID NO:12 and SEQ ID NO:13, respectively.

An additional sequence isolated as an EST (SEQ ID NO:7) bore considerable homology to that of known acetyl-coA acetyltransferases, but encoded a significantly shorter polypeptide (SEQ ID NO:14). The presence of a poly-(A) tail in the cDNA clone (SEQ ID NO:7) implies that this peptide is a genuine product of gene expression in *Hevea*. This short gene product may catalyse a similar reaction as the longer acetyl coA acetyltransferase (SEQ ID NO:1) and thus may also be involved in IPP synthesis in *Hevea*. However, no homolog as short as this could be identified in internal or external databases, thus this identification remains speculative. In conclusion, a set of *Hevea brasiliensis* cDNAs have been identified as most likely encoding enzymes involved in IPP synthesis by homology with known gene products.

What is claimed is:

1. An isolated polynucleotide comprising:
   (a) a nucleotide sequence encoding a polypeptide having acetyl-coA acetyltransferase activity, wherein the polypeptide has an amino acid sequence of at least 95% sequence identity, based on the Clustal method of alignment, when compared to SEQ ID NO:8, or
   (b) a full-length complement of the nucleotide sequence of (a).

2. The polynucleotide of claim 1, wherein the amino acid sequence of the polypeptide comprises SEQ ID NO:8.

3. The polynucleotide of claim 1 wherein the nucleotide sequence comprises SEQ ID NO:1.

4. A vector comprising the polynucleotide of claim 1.

5. A recombinant DNA construct comprising the polynucleotide of claim 1 operably linked to at least one heterologous regulatory sequence.

6. A method for transforming a cell, comprising transforming a cell with the polynucleotide of claim 1.

7. A cell comprising the recombinant DNA construct of claim 5.

8. A method for producing a plant comprising transforming a plant cell with the polynucleotide of claim 1 and regenerating a plant from the transformed plant cell.

9. A plant comprising the recombinant DNA construct of claim 5.

10. A seed comprising the recombinant DNA construct of claim 5.

* * * * *

SEQUENCE LISTING

```
<160> NUMBER OF SEQ ID NOS: 16

<210> SEQ ID NO 1
<211> LENGTH: 1233
<212> TYPE: DNA
<213> ORGANISM: Hevea brasiliensis
```

```
<400> SEQUENCE: 1
atgtctcctt cttcagattc tataaacccg cgagatgttt gtatcgtggg tgttgctcgt      60
acgcctatgg gtggctttct tggttctctt tcttccttct cagctacaaa actcggttcc     120
atagctattc aggctgctct taaaagggca aacgtcgatc catctcttgt ccaagaggtc     180
ttctttggca atgttctcag tgctaattta ggacaagctc ctgcaaggca ggctgcttta     240
ggtgcgggta tacccaattc agtgatttgt accaccatta taaagtttg tgcatcgggg     300 atgaaagcta ctatgcttgc tgcactgact attcaagtgg gtatcaatga tattgttgtg     360
gctggtggaa tggaaagcat gtctaacgcg cccaaatatc ttgcagaagc aagaagggga     420
tctcgactag gacatgatac cattattgat ggcatgctga agatggcct gtgggatgta     480 tataatgact ttggaatggg agtttgtgca gaaatatgtg ctgatcaaca taatattacg     540
agagaagaaa aggattctta tgccattcgg agctttgaac gtggaaattc tgcacaaaat     600
ggtggtgttt tttcctggga aatagttcct gttgaagttt ctggggacg agggaaatca     660 gttatggttg ttgacaagga cgaaggttta ataaagtttg atgctgccaa actgaggaaa     720
ctcagaccaa tttcaagaat tggttcggtt acagctggaa atgcttctat cataagtgat     780
ggtgcagctg cattagtcct ggtgagcgga gaaaaggcaa ttgagcttgg attgcaagtg     840
attgctagga taagaggata tggtgatgct gctcaggccc tgagttatt tacaacagca     900 ccagcacttg cgataccaaa agctatttca aatgctgggt ggaggcttc ccagattgat     960 tattatgaaa taaatgaagc attttctgtt gtggcccttg ccaatcaaaa gatacttggt    1020
cttaatcctg aaaaattaaa tgttcatgga ggagctgtat ctttgggaca tccattagga    1080
tgcagtggag ctcgtatctt ggtcacatta ttagggtac ttagacataa aaatggtaag    1140
tatggggttg ctagcatttg caatggaggt ggaggggcat ctgcccttgt tcttgagctc    1200
atgtcagttg aagggtggg acgttcgttg tta                                   1233

<210> SEQ ID NO 2
<211> LENGTH: 1392
<212> TYPE: DNA
<213> ORGANISM: Hevea brasiliensis

<400> SEQUENCE: 2
atggcaaaga atgtgggaat ctcgctgtg gacatctact ttcctcctac ctttgttcag       60
caggaagcac tggaggctca tgatggtgca agcaaaggga atacaccat tggacttgga     120 caggattgca tggcattttg tactgagtg gaagatgtca tctcaatgag tttgactgca     180
gttacttcac tcctcgacaa gtataatatt gatcctaaac aaatcggtcg tctggaagtt    240
ggcagtgaga ctgtgatcga caagagcaaa tctattaaaa ccttcttgat gcaaattttc     300
gagaaattcg gaaacactga cattgaaggc gttgactcaa caaatgcatg ttatggggg     360 actgcagctt tattcaactg tgtcaattgg gttgagagca gttcatggga tggacgctat    420
ggacttgtag tgtgtactga cagtgcggtc tatgcagagg gtccagcccg accaactgga    480
ggagctgcag ccattgcgat ttagtaggt ccagatgcac ctattgcttt tgaaagcaaa    540
tttaggggga gccatatgtc tcatgcttat gattttaca agcccaacct ggctagtgaa     600
tatccagttg tggatggcaa gctttcccaa acatgctacc tcatggctct tgattcttgc    660
tacaaacatt tctgtgccaa gtatgagaaa tttgaaggca agcaattctc tatttctgat    720
gctgaatatt ttgtatttca ttctccttac aacaagcttg tacagaaaag ctttgctcgt    780
ttggtgttca atgactttgt gaggaatgcc agctctattg atgagactgc taagaaaag    840
```

| | |
|---|---|
| ctggcaccgt tttcaaattt atctggtgat gaaagctacc aaaaccggga tcttgaaaag | 900 |
| gtatcccaac aagttgccaa gcccctttat gatgcgaaag tgaaaccaac cactttgata | 960 |
| ccaaagcaag ttggcaatat gtacactgca tctttgtatg cagcatttgc atccctcctt | 1020 |
| cacagtaaac atactgaatt ggcaggcaag cgggtgacac tgttctctta tgggagtggg | 1080 |
| ttgacagcca caatgttctc attgcgacta catgaaggcc aacatcccctt tagcttgtca | 1140 |
| aacattgcat ctgtgatgaa tgttgcagga agttgaagg caagacatga gcttccccca | 1200 |
| gagaagtttg tagacatcat gaagctaatg gagcaccggt acggagctaa agactttgtg | 1260 |
| acaagcaagg attgcagcct cttggcttct ggaacatact atctcacaga agttgacagc | 1320 |
| ttgtatcgaa gattctatgc ccagaaggct gttggcaaca cagttgagaa tggtttgctg | 1380 |
| gctaatggtc at | 1392 |

<210> SEQ ID NO 3
<211> LENGTH: 1974
<212> TYPE: DNA
<213> ORGANISM: Hevea brasiliensis

<400> SEQUENCE: 3

| | |
|---|---|
| atggacacca ccggccggct ccaccaccga aagcatgcta cacccgttga ggaccgttct | 60 |
| ccgaccactc cgaaagcgtc ggacgcgctt ccgcttcccc tctacctgac caacgcggtt | 120 |
| ttcttcacgc tgttcttctc ggtggcgtat acctccttc accggtggcg cgacaagatc | 180 |
| cgcaactcca ctccccttca tatcgttact ctctctgaaa ttgttgctat tgtctccctc | 240 |
| attgcctctt tcatttacct cctaggattc ttcggtatcg attttgtgca gtcattcatt | 300 |
| gcacgcgcct cccatgacgt gtgggacctc gaagatacgg atcccaacta cctcatcgat | 360 |
| gaagatcacc gtctcgttac ttgccctccc gctaatatat ctactaagac taccattatt | 420 |
| gccgcaccta ccaaattgcc tacctcggaa cccttaattg caccctagt ctcggaggaa | 480 |
| gacgaaatga tcgtcaactc cgtcgtggat gggaagatac cctcctattc tctggagtcg | 540 |
| aagctcgggg actgcaaacg agcggctgcg attcgacgcg aggctttgca gaggatgaca | 600 |
| aggaggtcgc tggaaggctt gccagtagaa gggttcgatt acgagtcgat tttaggacaa | 660 |
| tgctgtgaaa tgccagtggg atacgtgcag attccggtgg ggattgcggg gccgttgttg | 720 |
| ctgaacggcc gggagtactc tgttccaatg gcgaccacgg agggttgttt ggtggcgagc | 780 |
| actaatagag ggtgtaaggc catttacttg tcaggtgggg ccaccagcgt tttgttgaag | 840 |
| gatggcatga caagagcgcc tgttgttaga ttcgcgtcgg cgactagagc cgcggagttg | 900 |
| aagttcttct tggaggatcc tgacaatttt gataccttgg ccgtagtttt taacaagtct | 960 |
| agtagatttg cgaggctcca aggcattaaa tgctcaattg ctggtaagaa tctttatata | 1020 |
| agattcagct gcagcactgg cgatgcaatg gggatgaaca tggtttctaa aggggttcaa | 1080 |
| aacgttcttg aatttcttca agtgattttt tctgatatgg atgtcattgg catctcagga | 1140 |
| aattttttgtt cggataagaa gcctgctgct gtaaattgga ttgaaggacg tggcaaatca | 1200 |
| gttgtttgtg aggcaattat caaggaagag gtggtgaaga agtgtgttgaa aaccaatgtg | 1260 |
| gcctccctag tggagcttaa catgctcaag aatcttgctg ttctgctgt tgctggtgct | 1320 |
| ttgggtggat ttaatgccca tgcaggcaac atcgtatctg caatctttat tgccactggc | 1380 |
| caggatccag cacagaatgt tgagagttct cattgcatta ccatgatgga agctgtcaat | 1440 |
| gatggaaagg atctccatat ctctgtgacc atgccctcca ttgaggtggg tacagtcgga | 1500 |
| ggtggaactc aacttgcatc tcagtctgct tgtctcaatt gcttggggt gaagggtgca | 1560 |

-continued

```
aacaaagagt cgccaggatc aaactcaagg ctccttgctg ccatcgtagc tggttcagtt    1620
ttggctggtg agctctcctt gatgtctgcc attgcagctg ggcagcttgt caagagtcac    1680
atgaagtaca acagatccag caaagatatg tctaaagctg catcttagtg ggaatctggt    1740
cccagcaatg taaaatgatc taaaataaaa tgtggcggag attgtttggg agagagagag    1800
aggaagggag ggatagagag agagagagag agagagagag tgaggggaaa agtcaaggc     1860 tgattggttc ccatgtggga ttgtttagct gtcatagctg taaaatttgc tgttatatga    1920
agtatggaga taggaatgaa gcattgctaa tcatgctttg cctctccttc ttcc          1974
```

<210> SEQ ID NO 4
<211> LENGTH: 1158
<212> TYPE: DNA
<213> ORGANISM: Hevea brasiliensis
<400> SEQUENCE: 4

```
atggaagtta aagcaagagc tccagggaaa atcattctct ccggtgaaca cgcagtggtg      60
cacggatcca ctgcagtcgc tgcatccatt aatctctaca cctatgtcac cctttctttt     120
gctactgctg agaatgatga ttcactgaaa cttcagctca aggatctggc actagaattt     180
tcatggccaa ttggtagaat cagagaggca ttatctaact taggtgctcc ttcctcttca     240
acacgcacct cttgctcgat ggaatcaatt aagacaattt cagctttggt tgaagaagaa     300
aatatcccag aggcaaaaat tgcactcact tctggagtgt cagcctttttt atggttatat    360 acttctattc aaggatttaa gcctgccacc gtagttgtca cttctgatct tccactgggt     420
tcaggcctag gatcatctgc tgcattttgt gttgccctct cagctgctct gcttgctttc     480
tcagactctg taaatgtgga cacaaagcac ctagggtggt caatatttgg agagtctgac     540
cttgaattat taaacaaatg ggctctcgaa ggtgaaaaga taattcatgg aaagccatct     600
ggaatagaca cactgtcag cgcatatggc aacatgatca gttcaagtc tggtaatctg      660 actcgcatca agtccaacat gccgctcaaa atgctcgtca ctaacacaag agttgggagg     720
aacacaaaag cactggttgc tggtgtttca gagagaaccct tacggcaccc taatgccatg    780
agttttgttt ttaatgccgt tgattctatc agtaatgagc tggctaacat catccagtca     840
cctgctccag atgatgtgtc cataactgag aaggaagaga agctagaaga gttaatggaa     900
atgaatcaag gcttgcttca atgcatgggg gtcagccatg cttctataga aactgttctt     960
cggacaactt tgaaatacaa gttagcttcc aagctgactg gagcagggggg tgggggggtgc   1020 gtgctgacac tgttaccaac cctgctatca ggaacagttg ttgacaaagc aattgctgaa    1080
ttggagtcat gcggatttca atgtttgatt gctggaatcg gtgggaatgg tgttgagttt    1140
tgctttggtg gttcatcc                                                  1158
```

<210> SEQ ID NO 5
<211> LENGTH: 1509
<212> TYPE: DNA
<213> ORGANISM: Hevea brasiliensis
<400> SEQUENCE: 5

```
atggctgtag ttgcttctgc tccgggtaag gtgttgatga ctgggggtta cctcatattg      60
gaaagaccca atgcagggat tgtactcagc acaaatgctc gattctatgc cattgtgaag    120
cctatttacg atgaaatcaa acctgatagt tgggcatggg catggactga tgtgaaatta    180
acatctcccc aactagcaag ggaaagcttg tacaaattgt cactgaaaaa tttagctctt     240
cagtgtgtct cttcaagtgc atcaaggaac ccatttgtgg aacaagcagt gcaatttgct    300
```

```
gtagcagctg cacatgcaac acttgacaaa gataagaaga atgtcttaaa caagctactc      360
ttgcaaggtc ttgatattac aatattaggt accaatgact tctattcata ccgaaatgag      420
attgaagcat gtggactccc tttgacacca gaatcattgg ctgcacttcc ttctttttcc      480
tcaatcacct tcaatgtaga ggaagcaaat ggacaaaact gcaagcctga ggtagctaaa      540
actggattgg gttcatcagc agcaatgacc actgctgtag ttgctgcttt acttcatcac      600
cttggattgg ttgatctttc atcctcttgt aaagagaaga aattttctga tcttgatttg      660
gtacatataa tagcccaaac tgcccattgt attgcacaag ggaaagtcgg cagtggattt      720
gatgttagtt ctgcagttta tggcagtcat cgatacgtgc gcttctctcc agaagtgctt      780
tcctctgctc aggatgctgg gaaaggaatt ccattacagg aagtcatttc taacatccta      840
aaaggaaaat gggaccatga gaggactatg ttttccttgc caccattgat gagcctgcta      900
ctaggtgagc caggaactgg aggatcttcc acgccatcaa tggtaggtgc tctaaagaaa      960
tggcagaagt ctgatactca gaatcccaa gaaacatgga gaaagttgtc agaggcaaat     1020
tcagcacttg aaacgcaatt caatatttta agcaagctcg cagaagaaca ttgggacgcg     1080
tataaatgtg tgatagacag ttgcagcaca aaaaactcag agaagtggat tgagcaggca     1140
actgaaccca gccgagaagc agttgttaaa gcattattag gatcaagaaa tgccatgctt     1200
cagatcagaa attacatgcg ccagatgggt gaggctgcag gtgttccgat agagcctgaa     1260
tcacagactc gacttttgga tactactatg aatatggatg gagtcttgtt ggctggagtt     1320
cctggagcag gtgggtttga tgcagtcttc gctgttacct taggggactc tggtaccaat     1380
gtggcaaaag cttggagttc actcaatgtt ctggccctgt tggttagaga agaccctaat     1440
ggtgttttgt tagaaagcgg cgatccaaga accaaggaaa tcacaacagc tgttttgca     1500 gttcatatt                                                            1509

<210> SEQ ID NO 6
<211> LENGTH: 1245
<212> TYPE: DNA
<213> ORGANISM: Hevea brasiliensis

<400> SEQUENCE: 6
atggcggagt catgggtgat aatggtgact gcgcagacac ctactaatat agcagtgata       60
aaatactggg ggaagaggga tgagaagctt attttacctg ttaatgatag cataagtgtt      120
actctggatc ctgcacatct ttgtactacc actactgttg ccgtcagtcc tagttttgct      180
caggatcgga tgtggcttaa tggaaaggag atttccctt ctgggggcag gtaccaaaat       240
tgtttaaggg aaattcgtgc tcgagcctgt gatgttgagg ataaagaaag gggtatcaag      300
atttcaaaga aggattggga gaaattgtat gtacatatag cttcatataa caatttccct      360
actgctgctg gattggcttc ttcagctgct ggttttgctt gtcttgtttt tgcccttgca      420
aagctgatga atgctaaaga agataatagt gagctttctg ctattgcaag acaaggttca      480
ggcagtgctt gtcgtagttt gtttggtgga tttgtgaagt ggaaaatggg aaaggttgag      540 gatgaagtg acagccttgc tgttcaagtt gtagatgaga agcactggga tgatcttgtt      600
attattattg ctgtggtaag ttcacggcag aaagaaacga gtagcaccac aggaatgcgt      660
gagactgtta aaccagcctt gcttttgcaa catagagcta aggagatagt accaaaacgc      720
attgtacaaa tggaagagtc cataaaaaac cgcaattttg catcttttgc acacttaaca      780
tgtgctgata gtaaccagtt ccatgctgtc tgcatggata catgtcctcc aattttctac      840
atgaacgata catcacacag gataatcagc tgtgttgaaa aatggaatcg ttctgtagga      900
```

-continued

```
acacctcagg tggcttatac ttttgatgct gggcctaatg cagttctaat tgcacataat     960
aggaaggccg ctgcccagtt actgcagaag ctgcttttct atttccctcc aaattctgat    1020
actgaattaa acagttatgt tcttggtgat aagtcaatac taaaagatgc tgggattgaa    1080
gatttgaagg atgtggaagc attgccacca cctccagaaa ttaaagatgc cccaagatac    1140 aaagggatg ttagttattt catctgtaca agaccaggcc agggtccggt tttgctctct    1200
gatgaaagtc aggctctcct cagccctgaa actgggctcc ctaaa                    1245
```

<210> SEQ ID NO 7
<211> LENGTH: 696
<212> TYPE: DNA
<213> ORGANISM: Hevea brasiliensis

<400> SEQUENCE: 7

```
atggccccag cagcagcaac agcagtagcg gcagaaataa agcctagaga tgtttgcatt      60
gttggtgttg cccgcacacc gatgggtgga tttcttggtt cgctatgtac tttatctgcc    120
accaaactgg gatctatagc cattgaagct gctcttaaaa gggctaatgt tgatccatca    180
cttgtacaag aagttttctt tggaaatgtt ctcagtgcta atttagggca ggctcctgct    240
agacaggctg cattaggtgc aggaattcct aattcagtgg tctgtaccac tgttaacaaa    300
gtttgtgctt cggggatgaa agcaactatg cttgcagccc agagtatcca gttaggcatc    360
aatgatgttg ttgttgctgg aggcatggag agcatgtcca atgcacctaa atacctagca    420
gaagcaagga agggatctcg acttggacat gattcactag ttgatggaat gctgaaagat    480
gggttgtggg atgtttataa tgatgttggc atgggaagtt gtgctgaaat atgtgctgat    540
aatcattcaa taacgaggga ggatcaggat aaatttgcta ttcacagttt tgaacgcggt    600
attgctgcac aagaaagtgg tgcctttgca tgggaaattg ttccggttga agtttcgaag    660
gggcaaggag gaaactatga ctggcatgtg ggttgt                               696
```

<210> SEQ ID NO 8
<211> LENGTH: 411
<212> TYPE: PRT
<213> ORGANISM: Hevea brasiliensis

<400> SEQUENCE: 8

```
Met Ser Pro Ser Ser Asp Ser Ile Asn Pro Arg Asp Val Cys Ile Val
  1               5                  10                  15

Gly Val Ala Arg Thr Pro Met Gly Gly Phe Leu Gly Ser Leu Ser Ser
             20                  25                  30

Phe Ser Ala Thr Lys Leu Gly Ser Ile Ala Ile Gln Ala Ala Leu Lys
         35                  40                  45

Arg Ala Asn Val Asp Pro Ser Leu Val Gln Glu Val Phe Phe Gly Asn
     50                  55                  60

Val Leu Ser Ala Asn Leu Gly Gln Ala Pro Ala Arg Gln Ala Ala Leu
 65                  70                  75                  80

Gly Ala Gly Ile Pro Asn Ser Val Ile Cys Thr Thr Ile Asn Lys Val
                 85                  90                  95

Cys Ala Ser Gly Met Lys Ala Thr Met Leu Ala Ala Leu Thr Ile Gln
            100                 105                 110

Val Gly Ile Asn Asp Ile Val Val Ala Gly Gly Met Glu Ser Met Ser
        115                 120                 125

Asn Ala Pro Lys Tyr Leu Ala Glu Ala Arg Arg Gly Ser Arg Leu Gly
    130                 135                 140
```

```
His Asp Thr Ile Ile Asp Gly Met Leu Lys Asp Gly Leu Trp Asp Val
145                 150                 155                 160

Tyr Asn Asp Phe Gly Met Gly Val Cys Ala Glu Ile Cys Ala Asp Gln
                165                 170                 175

His Asn Ile Thr Arg Glu Glu Lys Asp Ser Tyr Ala Ile Arg Ser Phe
            180                 185                 190

Glu Arg Gly Asn Ser Ala Gln Asn Gly Gly Val Phe Ser Trp Glu Ile
        195                 200                 205

Val Pro Val Glu Val Ser Gly Arg Gly Lys Ser Val Met Val Val
    210                 215                 220

Asp Lys Asp Glu Gly Leu Ile Lys Phe Asp Ala Ala Lys Leu Arg Lys
225                 230                 235                 240

Leu Arg Pro Ile Ser Arg Ile Gly Ser Val Thr Ala Gly Asn Ala Ser
                245                 250                 255

Ile Ile Ser Asp Gly Ala Ala Ala Leu Val Leu Val Ser Gly Glu Lys
                260                 265                 270

Ala Ile Glu Leu Gly Leu Gln Val Ile Ala Arg Ile Arg Gly Tyr Gly
            275                 280                 285

Asp Ala Ala Gln Ala Pro Glu Leu Phe Thr Thr Ala Pro Ala Leu Ala
290                 295                 300

Ile Pro Lys Ala Ile Ser Asn Ala Gly Leu Glu Ala Ser Gln Ile Asp
305                 310                 315                 320

Tyr Tyr Glu Ile Asn Glu Ala Phe Ser Val Ala Leu Ala Asn Gln
                325                 330                 335

Lys Ile Leu Gly Leu Asn Pro Glu Lys Leu Asn Val His Gly Gly Ala
                340                 345                 350

Val Ser Leu Gly His Pro Leu Gly Cys Ser Gly Ala Arg Ile Leu Val
            355                 360                 365

Thr Leu Leu Gly Val Leu Arg His Lys Asn Gly Lys Tyr Gly Val Ala
    370                 375                 380

Ser Ile Cys Asn Gly Gly Gly Gly Ala Ser Ala Leu Val Leu Glu Leu
385                 390                 395                 400

Met Ser Val Gly Arg Val Gly Arg Ser Leu Leu
                405                 410

<210> SEQ ID NO 9
<211> LENGTH: 464
<212> TYPE: PRT
<213> ORGANISM: Hevea brasiliensis

<400> SEQUENCE: 9

Met Ala Lys Asn Val Gly Ile Leu Ala Val Asp Ile Tyr Phe Pro Pro
1               5                   10                  15

Thr Phe Val Gln Gln Glu Ala Leu Glu Ala His Asp Gly Ala Ser Lys
                20                  25                  30

Gly Lys Tyr Thr Ile Gly Leu Gly Gln Asp Cys Met Ala Phe Cys Thr
            35                  40                  45

Glu Val Glu Asp Val Ile Ser Met Ser Leu Thr Ala Val Thr Ser Leu
        50                  55                  60

Leu Asp Lys Tyr Asn Ile Asp Pro Lys Gln Ile Gly Arg Leu Glu Val
65                  70                  75                  80

Gly Ser Glu Thr Val Ile Asp Lys Ser Lys Ser Ile Lys Thr Phe Leu
                85                  90                  95

Met Gln Ile Phe Glu Lys Phe Gly Asn Thr Asp Ile Glu Gly Val Asp
                100                 105                 110
```

```
Ser Thr Asn Ala Cys Tyr Gly Gly Thr Ala Ala Leu Phe Asn Cys Val
        115                 120                 125

Asn Trp Val Glu Ser Ser Trp Asp Gly Arg Tyr Gly Leu Val Val
    130                 135                 140

Cys Thr Asp Ser Ala Val Tyr Ala Glu Gly Pro Ala Arg Pro Thr Gly
145                 150                 155                 160

Gly Ala Ala Ile Ala Ile Leu Val Gly Pro Asp Ala Pro Ile Ala
                165                 170                 175

Phe Glu Ser Lys Phe Arg Gly Ser His Met Ser His Ala Tyr Asp Phe
                180                 185                 190

Tyr Lys Pro Asn Leu Ala Ser Glu Tyr Pro Val Val Asp Gly Lys Leu
            195                 200                 205

Ser Gln Thr Cys Tyr Leu Met Ala Leu Asp Ser Cys Tyr Lys His Phe
    210                 215                 220

Cys Ala Lys Tyr Glu Lys Phe Glu Gly Lys Gln Phe Ser Ile Ser Asp
225                 230                 235                 240

Ala Glu Tyr Phe Val Phe His Ser Pro Tyr Asn Lys Leu Val Gln Lys
                245                 250                 255

Ser Phe Ala Arg Leu Val Phe Asn Asp Phe Val Arg Asn Ala Ser Ser
            260                 265                 270

Ile Asp Glu Thr Ala Lys Glu Lys Leu Ala Pro Phe Ser Asn Leu Ser
    275                 280                 285

Gly Asp Glu Ser Tyr Gln Asn Arg Asp Leu Glu Lys Val Ser Gln Gln
290                 295                 300

Val Ala Lys Pro Leu Tyr Asp Ala Lys Val Lys Pro Thr Thr Leu Ile
305                 310                 315                 320

Pro Lys Gln Val Gly Asn Met Tyr Thr Ala Ser Leu Tyr Ala Ala Phe
                325                 330                 335

Ala Ser Leu Leu His Ser Lys His Thr Glu Leu Ala Gly Lys Arg Val
                340                 345                 350

Thr Leu Phe Ser Tyr Gly Ser Gly Leu Thr Ala Thr Met Phe Ser Leu
            355                 360                 365

Arg Leu His Glu Gly Gln His Pro Phe Ser Leu Ser Asn Ile Ala Ser
    370                 375                 380

Val Met Asn Val Ala Gly Lys Leu Lys Ala Arg His Glu Leu Pro Pro
385                 390                 395                 400

Glu Lys Phe Val Asp Ile Met Lys Leu Met Glu His Arg Tyr Gly Ala
                405                 410                 415

Lys Asp Phe Val Thr Ser Lys Asp Cys Ser Leu Leu Ala Ser Gly Thr
                420                 425                 430

Tyr Tyr Leu Thr Glu Val Asp Ser Leu Tyr Arg Arg Phe Tyr Ala Gln
            435                 440                 445

Lys Ala Val Gly Asn Thr Val Glu Asn Gly Leu Leu Ala Asn Gly His
    450                 455                 460

<210> SEQ ID NO 10
<211> LENGTH: 575
<212> TYPE: PRT
<213> ORGANISM: Hevea brasiliensis

<400> SEQUENCE: 10

Met Asp Thr Thr Gly Arg Leu His His Arg Lys His Ala Thr Pro Val
1               5                   10                  15

Glu Asp Arg Ser Pro Thr Thr Pro Lys Ala Ser Asp Ala Leu Pro Leu
            20                  25                  30
```

```
Pro Leu Tyr Leu Thr Asn Ala Val Phe Phe Thr Leu Phe Phe Ser Val
        35                  40                  45

Ala Tyr Tyr Leu Leu His Arg Trp Arg Asp Lys Ile Arg Asn Ser Thr
 50                  55                  60

Pro Leu His Ile Val Thr Leu Ser Glu Ile Val Ala Ile Val Ser Leu
 65                  70                  75                  80

Ile Ala Ser Phe Ile Tyr Leu Leu Gly Phe Phe Gly Ile Asp Phe Val
                 85                  90                  95

Gln Ser Phe Ile Ala Arg Ala Ser His Asp Val Trp Asp Leu Glu Asp
                100                 105                 110

Thr Asp Pro Asn Tyr Leu Ile Asp Glu Asp His Arg Leu Val Thr Cys
            115                 120                 125

Pro Pro Ala Asn Ile Ser Thr Lys Thr Thr Ile Ala Ala Pro Thr
130                 135                 140

Lys Leu Pro Thr Ser Glu Pro Leu Ile Ala Pro Leu Val Ser Glu Glu
145                 150                 155                 160

Asp Glu Met Ile Val Asn Ser Val Val Asp Gly Lys Ile Pro Ser Tyr
                165                 170                 175

Ser Leu Glu Ser Lys Leu Gly Asp Cys Lys Arg Ala Ala Ala Ile Arg
            180                 185                 190

Arg Glu Ala Leu Gln Arg Met Thr Arg Arg Ser Leu Glu Gly Leu Pro
            195                 200                 205

Val Glu Gly Phe Asp Tyr Glu Ser Ile Leu Gly Gln Cys Cys Glu Met
            210                 215                 220

Pro Val Gly Tyr Val Gln Ile Pro Val Gly Ile Ala Gly Pro Leu Leu
225                 230                 235                 240

Leu Asn Gly Arg Glu Tyr Ser Val Pro Met Ala Thr Thr Glu Gly Cys
                245                 250                 255

Leu Val Ala Ser Thr Asn Arg Gly Cys Lys Ala Ile Tyr Leu Ser Gly
            260                 265                 270

Gly Ala Thr Ser Val Leu Leu Lys Asp Gly Met Thr Arg Ala Pro Val
            275                 280                 285

Val Arg Phe Ala Ser Ala Thr Arg Ala Ala Glu Leu Lys Phe Phe Leu
            290                 295                 300

Glu Asp Pro Asp Asn Phe Asp Thr Leu Ala Val Val Phe Asn Lys Ser
305                 310                 315                 320

Ser Arg Phe Ala Arg Leu Gln Gly Ile Lys Cys Ser Ile Ala Gly Lys
            325                 330                 335

Asn Leu Tyr Ile Arg Phe Ser Cys Ser Thr Gly Asp Ala Met Gly Met
            340                 345                 350

Asn Met Val Ser Lys Gly Val Gln Asn Val Leu Glu Phe Leu Gln Ser
            355                 360                 365

Asp Phe Ser Asp Met Asp Val Ile Gly Ile Ser Gly Asn Phe Cys Ser
            370                 375                 380

Asp Lys Lys Pro Ala Ala Val Asn Trp Ile Glu Gly Arg Gly Lys Ser
385                 390                 395                 400

Val Val Cys Glu Ala Ile Ile Lys Glu Glu Val Val Lys Lys Val Leu
                405                 410                 415

Lys Thr Asn Val Ala Ser Leu Val Glu Leu Asn Met Leu Lys Asn Leu
                420                 425                 430

Ala Gly Ser Ala Val Ala Gly Ala Leu Gly Gly Phe Asn Ala His Ala
            435                 440                 445
```

```
Gly Asn Ile Val Ser Ala Ile Phe Ile Ala Thr Gly Gln Asp Pro Ala
    450                 455                 460

Gln Asn Val Glu Ser Ser His Cys Ile Thr Met Met Glu Ala Val Asn
465                 470                 475                 480

Asp Gly Lys Asp Leu His Ile Ser Val Thr Met Pro Ser Ile Glu Val
                485                 490                 495

Gly Thr Val Gly Gly Thr Gln Leu Ala Ser Gln Ser Ala Cys Leu
            500                 505                 510

Asn Leu Leu Gly Val Lys Gly Ala Asn Lys Glu Ser Pro Gly Ser Asn
            515                 520                 525

Ser Arg Leu Leu Ala Ala Ile Val Ala Gly Ser Val Leu Ala Gly Glu
    530                 535                 540

Leu Ser Leu Met Ser Ala Ile Ala Ala Gly Gln Leu Val Lys Ser His
545                 550                 555                 560

Met Lys Tyr Asn Arg Ser Ser Lys Asp Met Ser Lys Ala Ala Ser
                565                 570                 575

<210> SEQ ID NO 11
<211> LENGTH: 386
<212> TYPE: PRT
<213> ORGANISM: Hevea brasiliensis

<400> SEQUENCE: 11

Met Glu Val Lys Ala Arg Ala Pro Gly Lys Ile Ile Leu Ser Gly Glu
1               5                   10                  15

His Ala Val Val His Gly Ser Thr Ala Val Ala Ala Ser Ile Asn Leu
                20                  25                  30

Tyr Thr Tyr Val Thr Leu Ser Phe Ala Thr Ala Glu Asn Asp Asp Ser
            35                  40                  45

Leu Lys Leu Gln Leu Lys Asp Leu Ala Leu Glu Phe Ser Trp Pro Ile
    50                  55                  60

Gly Arg Ile Arg Glu Ala Leu Ser Asn Leu Gly Ala Pro Ser Ser Ser
65                  70                  75                  80

Thr Arg Thr Ser Cys Ser Met Glu Ser Ile Lys Thr Ile Ser Ala Leu
                85                  90                  95

Val Glu Glu Asn Ile Pro Glu Ala Lys Ile Ala Leu Thr Ser Gly
                100                 105                 110

Val Ser Ala Phe Leu Trp Leu Tyr Thr Ser Ile Gln Gly Phe Lys Pro
            115                 120                 125

Ala Thr Val Val Val Thr Ser Asp Leu Pro Leu Gly Ser Gly Leu Gly
    130                 135                 140

Ser Ser Ala Ala Phe Cys Val Ala Leu Ser Ala Ala Leu Leu Ala Phe
145                 150                 155                 160

Ser Asp Ser Val Asn Val Asp Thr Lys His Leu Gly Trp Ser Ile Phe
                165                 170                 175

Gly Glu Ser Asp Leu Glu Leu Leu Asn Lys Trp Ala Leu Glu Gly Glu
            180                 185                 190

Lys Ile Ile His Gly Lys Pro Ser Gly Ile Asp Asn Thr Val Ser Ala
    195                 200                 205

Tyr Gly Asn Met Ile Lys Phe Lys Ser Gly Asn Leu Thr Arg Ile Lys
            210                 215                 220

Ser Asn Met Pro Leu Lys Met Leu Val Thr Asn Thr Arg Val Gly Arg
225                 230                 235                 240

Asn Thr Lys Ala Leu Val Ala Gly Val Ser Glu Arg Thr Leu Arg His
                245                 250                 255
```

```
Pro Asn Ala Met Ser Phe Val Phe Asn Ala Val Asp Ser Ile Ser Asn
        260                 265                 270

Glu Leu Ala Asn Ile Ile Gln Ser Pro Ala Pro Asp Val Ser Ile
        275                 280                 285

Thr Glu Lys Glu Lys Leu Glu Glu Leu Met Glu Met Asn Gln Gly
        290                 295                 300

Leu Leu Gln Cys Met Gly Val Ser His Ala Ser Ile Glu Thr Val Leu
305                 310                 315                 320

Arg Thr Thr Leu Lys Tyr Lys Leu Ala Ser Lys Leu Thr Gly Ala Gly
                325                 330                 335

Gly Gly Gly Cys Val Leu Thr Leu Leu Pro Thr Leu Leu Ser Gly Thr
                340                 345                 350

Val Val Asp Lys Ala Ile Ala Glu Leu Glu Ser Cys Gly Phe Gln Cys
                355                 360                 365

Leu Ile Ala Gly Ile Gly Gly Asn Gly Val Glu Phe Cys Phe Gly Gly
        370                 375                 380

Ser Ser
385

<210> SEQ ID NO 12
<211> LENGTH: 503
<212> TYPE: PRT
<213> ORGANISM: Hevea brasiliensis

<400> SEQUENCE: 12

Met Ala Val Val Ala Ser Ala Pro Gly Lys Val Leu Met Thr Gly Gly
1               5                   10                  15

Tyr Leu Ile Leu Glu Arg Pro Asn Ala Gly Ile Val Leu Ser Thr Asn
                20                  25                  30

Ala Arg Phe Tyr Ala Ile Val Lys Pro Ile Tyr Asp Glu Ile Lys Pro
            35                  40                  45

Asp Ser Trp Ala Trp Ala Trp Thr Asp Val Lys Leu Thr Ser Pro Gln
    50                  55                  60

Leu Ala Arg Glu Ser Leu Tyr Lys Leu Ser Leu Lys Asn Leu Ala Leu
65                  70                  75                  80

Gln Cys Val Ser Ser Ala Ser Arg Asn Pro Phe Val Glu Gln Ala
                85                  90                  95

Val Gln Phe Ala Val Ala Ala His Ala Thr Leu Asp Lys Asp Lys
                100                 105                 110

Lys Asn Val Leu Asn Lys Leu Leu Gln Gly Leu Asp Ile Thr Ile
        115                 120                 125

Leu Gly Thr Asn Asp Phe Tyr Ser Tyr Arg Asn Glu Ile Glu Ala Cys
130                 135                 140

Gly Leu Pro Leu Thr Pro Glu Ser Leu Ala Ala Leu Pro Ser Phe Ser
145                 150                 155                 160

Ser Ile Thr Phe Asn Val Glu Glu Ala Asn Gly Gln Asn Cys Lys Pro
                165                 170                 175

Glu Val Ala Lys Thr Gly Leu Gly Ser Ser Ala Ala Met Thr Thr Ala
            180                 185                 190

Val Val Ala Ala Leu Leu His His Leu Gly Leu Val Asp Leu Ser Ser
            195                 200                 205

Ser Cys Lys Glu Lys Lys Phe Ser Asp Leu Asp Leu Val His Ile Ile
    210                 215                 220

Ala Gln Thr Ala His Cys Ile Ala Gln Gly Lys Val Gly Ser Gly Phe
225                 230                 235                 240
```

```
Asp Val Ser Ser Ala Val Tyr Gly Ser His Arg Tyr Val Arg Phe Ser
            245                 250                 255

Pro Glu Val Leu Ser Ser Ala Gln Asp Ala Gly Lys Gly Ile Pro Leu
            260                 265                 270

Gln Glu Val Ile Ser Asn Ile Leu Lys Gly Lys Trp Asp His Glu Arg
            275                 280                 285

Thr Met Phe Ser Leu Pro Pro Leu Met Ser Leu Leu Gly Glu Pro
            290                 295                 300

Gly Thr Gly Gly Ser Ser Thr Pro Ser Met Val Gly Ala Leu Lys Lys
305                 310                 315                 320

Trp Gln Lys Ser Asp Thr Gln Lys Ser Gln Glu Thr Trp Arg Lys Leu
                325                 330                 335

Ser Glu Ala Asn Ser Ala Leu Glu Thr Gln Phe Asn Ile Leu Ser Lys
            340                 345                 350

Leu Ala Glu Glu His Trp Asp Ala Tyr Lys Cys Val Ile Asp Ser Cys
            355                 360                 365

Ser Thr Lys Asn Ser Glu Lys Trp Ile Glu Gln Ala Thr Glu Pro Ser
            370                 375                 380

Arg Glu Ala Val Val Lys Ala Leu Leu Gly Ser Arg Asn Ala Met Leu
385                 390                 395                 400

Gln Ile Arg Asn Tyr Met Arg Gln Met Gly Glu Ala Ala Gly Val Pro
                405                 410                 415

Ile Glu Pro Glu Ser Gln Thr Arg Leu Leu Asp Thr Thr Met Asn Met
            420                 425                 430

Asp Gly Val Leu Leu Ala Gly Val Pro Gly Ala Gly Gly Phe Asp Ala
            435                 440                 445

Val Phe Ala Val Thr Leu Gly Asp Ser Gly Thr Asn Val Ala Lys Ala
            450                 455                 460

Trp Ser Ser Leu Asn Val Leu Ala Leu Leu Val Arg Glu Asp Pro Asn
465                 470                 475                 480

Gly Val Leu Leu Glu Ser Gly Asp Pro Arg Thr Lys Glu Ile Thr Thr
                485                 490                 495

Ala Val Phe Ala Val His Ile
            500

<210> SEQ ID NO 13
<211> LENGTH: 415
<212> TYPE: PRT
<213> ORGANISM: Hevea brasiliensis

<400> SEQUENCE: 13

Met Ala Glu Ser Trp Val Ile Met Val Thr Ala Gln Thr Pro Thr Asn
1               5                   10                  15

Ile Ala Val Ile Lys Tyr Trp Gly Lys Arg Asp Glu Lys Leu Ile Leu
            20                  25                  30

Pro Val Asn Asp Ser Ile Ser Val Thr Leu Asp Pro Ala His Leu Cys
            35                  40                  45

Thr Thr Thr Thr Val Ala Val Ser Pro Ser Phe Ala Gln Asp Arg Met
            50                  55                  60

Trp Leu Asn Gly Lys Glu Ile Ser Leu Ser Gly Gly Arg Tyr Gln Asn
65                  70                  75                  80

Cys Leu Arg Glu Ile Arg Ala Arg Ala Cys Asp Val Glu Asp Lys Glu
                85                  90                  95

Arg Gly Ile Lys Ile Ser Lys Lys Asp Trp Glu Lys Leu Tyr Val His
            100                 105                 110
```

```
Ile Ala Ser Tyr Asn Asn Phe Pro Thr Ala Ala Gly Leu Ala Ser Ser
            115                 120                 125

Ala Ala Gly Phe Ala Cys Leu Val Phe Ala Leu Ala Lys Leu Met Asn
        130                 135                 140

Ala Lys Glu Asp Asn Ser Glu Leu Ser Ala Ile Ala Arg Gln Gly Ser
145                 150                 155                 160

Gly Ser Ala Cys Arg Ser Leu Phe Gly Gly Phe Val Lys Trp Lys Met
                165                 170                 175

Gly Lys Val Glu Asp Gly Ser Asp Ser Leu Ala Val Gln Val Val Asp
            180                 185                 190

Glu Lys His Trp Asp Asp Leu Val Ile Ile Ala Val Val Ser Ser
            195                 200                 205

Arg Gln Lys Glu Thr Ser Ser Thr Thr Gly Met Arg Glu Thr Val Glu
        210                 215                 220

Thr Ser Leu Leu Leu Gln His Arg Ala Lys Glu Ile Val Pro Lys Arg
225                 230                 235                 240

Ile Val Gln Met Glu Glu Ser Ile Lys Asn Arg Asn Phe Ala Ser Phe
                245                 250                 255

Ala His Leu Thr Cys Ala Asp Ser Asn Gln Phe His Ala Val Cys Met
            260                 265                 270

Asp Thr Cys Pro Pro Ile Phe Tyr Met Asn Asp Thr Ser His Arg Ile
        275                 280                 285

Ile Ser Cys Val Glu Lys Trp Asn Arg Ser Val Gly Thr Pro Gln Val
290                 295                 300

Ala Tyr Thr Phe Asp Ala Gly Pro Asn Ala Val Leu Ile Ala His Asn
305                 310                 315                 320

Arg Lys Ala Ala Gln Leu Leu Gln Lys Leu Leu Phe Tyr Phe Pro
                325                 330                 335

Pro Asn Ser Asp Thr Glu Leu Asn Ser Tyr Val Leu Gly Asp Lys Ser
            340                 345                 350

Ile Leu Lys Asp Ala Gly Ile Glu Asp Leu Lys Asp Val Glu Ala Leu
            355                 360                 365

Pro Pro Pro Glu Ile Lys Asp Ala Pro Arg Tyr Lys Gly Asp Val
        370                 375                 380

Ser Tyr Phe Ile Cys Thr Arg Pro Gly Gln Gly Pro Val Leu Leu Ser
385                 390                 395                 400

Asp Glu Ser Gln Ala Leu Leu Ser Pro Glu Thr Gly Leu Pro Lys
                405                 410                 415

<210> SEQ ID NO 14
<211> LENGTH: 232
<212> TYPE: PRT
<213> ORGANISM: Hevea brasiliensis

<400> SEQUENCE: 14

Met Ala Pro Ala Ala Ala Thr Ala Val Ala Ala Glu Ile Lys Pro Arg
1               5                   10                  15

Asp Val Cys Ile Val Gly Val Ala Arg Thr Pro Met Gly Gly Phe Leu
            20                  25                  30

Gly Ser Leu Cys Thr Leu Ser Ala Thr Lys Leu Gly Ser Ile Ala Ile
        35                  40                  45

Glu Ala Ala Leu Lys Arg Ala Asn Val Asp Pro Ser Leu Val Gln Glu
    50                  55                  60

Val Phe Phe Gly Asn Val Leu Ser Ala Asn Leu Gly Gln Ala Pro Ala
65                  70                  75                  80
```

```
Arg Gln Ala Ala Leu Gly Ala Gly Ile Pro Asn Ser Val Val Cys Thr
                85                  90                  95

Thr Val Asn Lys Val Cys Ala Ser Gly Met Lys Ala Thr Met Leu Ala
            100                 105                 110

Ala Gln Ser Ile Gln Leu Gly Ile Asn Asp Val Val Ala Gly Gly
            115                 120                 125

Met Glu Ser Met Ser Asn Ala Pro Lys Tyr Leu Ala Glu Ala Arg Lys
    130                 135                 140

Gly Ser Arg Leu Gly His Asp Ser Leu Val Asp Gly Met Leu Lys Asp
145                 150                 155                 160

Gly Leu Trp Asp Val Tyr Asn Asp Val Gly Met Gly Ser Cys Ala Glu
                165                 170                 175

Ile Cys Ala Asp Asn His Ser Ile Thr Arg Glu Asp Gln Asp Lys Phe
                180                 185                 190

Ala Ile His Ser Phe Glu Arg Gly Ile Ala Ala Gln Glu Ser Gly Ala
                195                 200                 205

Phe Ala Trp Glu Ile Val Pro Val Glu Val Ser Lys Gly Gln Gly Gly
    210                 215                 220

Asn Tyr Asp Trp His Val Gly Cys
225                 230

<210> SEQ ID NO 15
<211> LENGTH: 25
<212> TYPE: DNA
<213> ORGANISM: Artificial Sequence
<220> FEATURE:
<223> OTHER INFORMATION: Primer

<400> SEQUENCE: 15
acctacaaca aagctctcat caacc                                      25

<210> SEQ ID NO 16
<211> LENGTH: 25
<212> TYPE: DNA
<213> ORGANISM: Artificial Sequence
<220> FEATURE:
<223> OTHER INFORMATION: Primer

<400> SEQUENCE: 16
gcaatgtaac atcagagatt ttgag                                      25
```